United States Patent
Wu et al.

(10) Patent No.: US 12,180,303 B2
(45) Date of Patent: Dec. 31, 2024

(54) ANTI-HUMAN MASP-2 ANTIBODY, PREPARATION METHOD THEREFOR AND APPLICATION THEREOF

(71) Applicant: SHANGHAI MABGEEK BIOTECH. CO., LTD., Shanghai (CN)

(72) Inventors: Yipan Wu, Shanghai (CN); Wei Dang, Shanghai (CN); Chenghai Zhang, Shanghai (CN); Lingqiao Zhu, Shanghai (CN); Jinlin Guo, Shanghai (CN); Yujing Yuan, Shanghai (CN); Qiuling Zou, Shanghai (CN); Yang Wang, Shanghai (CN); Shun Hu, Shanghai (CN)

(73) Assignee: SHANGHAI MABGEEK BIOTECH. CO., LTD., Shanghai (CN)

(*) Notice: Subject to any disclaimer, the term of this patent is extended or adjusted under 35 U.S.C. 154(b) by 0 days.

(21) Appl. No.: 18/486,644

(22) Filed: Oct. 13, 2023

(65) Prior Publication Data

US 2024/0043563 A1 Feb. 8, 2024

Related U.S. Application Data

(63) Continuation of application No. PCT/CN2022/079499, filed on Mar. 7, 2022.

(30) Foreign Application Priority Data

Apr. 15, 2021 (CN) .......................... 202110404540.6

(51) Int. Cl.
    *C07K 16/40* (2006.01)
(52) U.S. Cl.
    CPC .......... *C07K 16/40* (2013.01); *C07K 2317/24* (2013.01); *C07K 2317/33* (2013.01); *C07K 2317/76* (2013.01); *C07K 2317/92* (2013.01)
(58) Field of Classification Search
    None
    See application file for complete search history.

(56) References Cited

U.S. PATENT DOCUMENTS

| | | | |
|---|---|---|---|
| 4,816,567 A | 3/1989 | Cabilly et al. | |
| 6,180,370 B1* | 1/2001 | Queen .................... | A61P 19/02 435/69.6 |
| 9,096,676 B2* | 8/2015 | Larsen .................... | A61P 19/02 |
| 9,475,885 B2 | 10/2016 | Dudler et al. | |
| 2013/0344073 A1 | 12/2013 | Schwaeble et al. | |

FOREIGN PATENT DOCUMENTS

| CN | 1798769 A | 7/2006 |
|---|---|---|
| CN | 107011443 A | 8/2017 |
| CN | 110177557 A | 8/2019 |
| CN | 111588855 A | 8/2020 |

OTHER PUBLICATIONS

Janeway CA Jr, Travers P, Walport M, et al. Immunobiology: The Immune System in Health and Disease.5th edition. New York: Garland Science; 2001 (Year: 2001).*

"Secondary Antibody Specific Binding Locations", Bio-Rad Antibodies, https://www.bio-rad-antibodies.com/secondary-antibody-binding-locations-benefits.html. Accessed Mar. 8, 2024. (Year: 2024).*

Gavriilaki, Eleni et al. "Role of the lectin pathway of complement in hematopoietic stem cell transplantation-associated endothelial injury and thrombotic microangiopathy." Experimental hematology & oncology vol. 10, 1 57. Dec. 19, 2021, doi: 10.1186/s40164-021-00249-8 (Year: 2021).*

Elhadad, S., et al. "MASP2 levels are elevated in thrombotic microangiopathies: association with microvascular endothelial cell injury and suppression by anti-MASP2 antibody narsoplimab." Clinical & Experimental Immunology 203.1 (2021): 96-104 (Year: 2021).*

Huang, Xin, and Gaosi Xu. "An Update on Targeted Treatment of IgA Nephropathy: An Autoimmune Perspective." Frontiers in pharmacology vol. 12 715253. Aug. 23, 2021, doi:10.3389/fphar.2021.715253 (Year: 2021).*

Kipriyanov, Sergey M., and Fabrice Le Gall. "Generation and production of engineered antibodies." Molecular biotechnology 26.1 (2004): 39-60. (Year: 2004).*

Janeway, Charles A. "Immunobiology: The Immune System in Health and Disease." 2001 (Year: 2001).*

May 26, 2022 International Search Report issued in International Patent Application No. PCT/CN2022/079499.

May 26, 2022 Written Opinion of the International Searching Authourity issued in International Patent Application No. PCT/CN2022/079499.

Chen. Huiping et al. Research Progress of Complement Abnormalities in IgA Nephropathy, Hainan Medical Journal, vol. 31. No. 06. Mar. 25, 2020 (Mar. 25, 2020).

Morrison SL, Johnson MJ, Herzenberg LA, Oi VT. Chimeric human antibody molecules: mouse antigen-binding domains with human constant region domains. Proceedings of the National Academy of Sciences of the United States of America. Nov. 1984; 81(21):6851-6855.

Martin A C R, Cheetham J C, Rees A R .Modeling Antibody Hypervariable Loops: A Combined Algorithm [J].Proceedings of the National Academy of Sciences, 1989, 86(23):9268-9272.

See Cheng Yeo, et al.New insights into the pathogenesis of IgA nephropathy [J].Pediatric Nephrology, 2018.

Kabat, E.A. Sequences of proteins of immunological interest. (1991).

(Continued)

*Primary Examiner* — Michael Szperka
*Assistant Examiner* — Lia E Taylor
(74) *Attorney, Agent, or Firm* — Harness, Dickey & Pierce, P.L.C.

(57) ABSTRACT

Disclosed are an antibody that can bind to human MASP-2, a preparation method therefor and an application thereof. The anti-human MASP-2 antibody of the present invention can specifically bind to human MASP-2, has good biological activity of inhibiting the cleavage of C4 and the generation of C3b, and can be applied in the treatment of MASP-2 related diseases, such as IgA nephropathy.

16 Claims, 3 Drawing Sheets

Specification includes a Sequence Listing.

(56) References Cited

OTHER PUBLICATIONS

Allazikani B, Lesk A M, Chothia C .Standard conformations for the canonical structures of immunoglobulins [J].Journal of Molecular Biology, 1997, 273(4):927-948.
Notice of Reasons for Refusal dated Oct. 1, 2024 Issued in Japanese application 2023-563126.
Lafayette RA, et al. Safety, Tolerability and Efficacy of Narsoplimab, a Novel MASP-2 Inhibitor for the Treatment of IgA Nepgropathy. Kidney Int Rep. Aug. 13, 2020;5(11):2032-2041.

* cited by examiner

ANTI-HUMAN MASP-2 ANTIBODY, PREPARATION METHOD THEREFOR AND APPLICATION THEREOF

CROSS-REFERENCE TO RELATED APPLICATIONS

This application is a continuation application of International Application No. PCT/CN2022/079499, filed on Mar. 7, 2022, which claims priority from Chinese Patent Application No. 202110404540.6 filed on Apr. 15, 2021, the entire contents of which are hereby incorporated by reference.

REFERENCE TO SEQUENCE LISTING

This application contains references to amino acid sequences and/or nucleic acid sequences which have been submitted concurrently herewith as the sequence listing .XML file entitled "00018lusco_SequenceListing.XML", file size 75 KiloBytes (KB), created on Oct. 11, 2023. The aforementioned sequence listing is hereby incorporated by reference in its entirety pursuant to 37 C.F.R. § 1.52(e)(5)

TECHNICAL FIELD

The present disclosure relates to the field of antibodies, and more specifically, the present disclosure relates to high-affinity antibodies specifically binding to human MASP-2, and a use of the antibodies as therapeutic agents, especially for MASP-2 related diseases. The diseases are, for example, atypical hemolytic uremic syndrome, hematopoietic stem cell transplantation-associated thrombotic microangiopathy (HSCT-TMA), and IgA nephropathy.

BACKGROUND

Complement system is an important factor for intrinsic immunity in a human body. The complement system is able to recognize and eliminate invading pathogenic microorganisms and to alter host cells through oposonization and lysis, and it is also capable of mounting an immune response to other acute injuries. Complement is a complex cascade system in which serine proteases activate each other in a strict sequence. It is now widely recognized that the complement system can be activated through three distinct pathways: classical pathway, lectin pathway, and alternative pathway.

There are approximately 120 million chronic kidney disease (CKD) patients in China, among which IgA nephropathy (IgAN) is the most common kidney disease. IgAN is also one of the primary glomerular diseases with the highest incidence worldwide, especially in Asian populations. The long-term prognosis of IgA nephropathy is poor, with 30 to 40% of patients progressing to end-stage renal disease (kidney failure) within 10 to 25 years. The etiology of IgA nephropathy is not yet fully understood. In the IgAN pathogenic model proposed by Yeo et al. (Yeo et al., *Pediatr Nephrol* 33:763-777, (2018)), it was noted that dysregulation of the mucosal immune system causes mucosal B cells to overproliferate, and mucosal B cells mistakenly entering the circulatory system allows secretion of IgA into the circulation, which in turn leads to elevated serum IgA levels. Accumulation of these IgA immune complexes in the glomerulus leads to activation of mesangial cells, release of pro-inflammatory and pro-fibrotic regulators, and activation of complement.

Increasing evidence that demonstrates glomerular injury in IgAN is associated with activation of the complement system makes inhibition of complement activation a promising approach for the treatment of IgAN. Studies have shown that alterations in the lectin pathway contribute to the development and progression of IgAN. Mannose-binding lectin-associated serine protease 2 (MASP-2), an effector enzyme necessary for the activation of the complement lectin pathway, is able to cleave complement component C4 to form C3 convertase C4b2b to activate complement, and is a potential drug target. Narsoplimab, an antibody developed by Omeros against the MASP-2 target, has now entered clinical phases II and III. The indications for this antibody are atypical hemolytic uremic syndrome, hematopoietic stem cell transplantation-associated thrombotic microangiopathy (HSCT-TMA), IgA nephropathy, lupus nephritis, and other renal diseases. Related patents include U.S. Pat. Nos. 9,096,676, 9,475,885, and US20130344073.

The present disclosure provides a novel antibody drug developed against new targets for diseases such as IgA nephropathy and lupus nephritis. The novel molecule of the present disclosure has the properties of high affinity, high potency, and excellent druggability.

SUMMARY

The inventors of the present disclosure, after having conducted a large number of experiments, obtained a group of high-affinity monoclonal antibodies specifically binding to human MASP-2. The antibody is able to inhibit the C4 enzymatic cleavage reaction of the lectin pathway and has the bioactivity to inhibit complement activation.

According to a first aspect, the present disclosure provides an antibody specifically binding to human MASP-2 or an antigen-binding fragment thereof, comprising a heavy chain variable region, wherein the heavy chain variable region comprises an HCDR3 sequence, and optionally further comprises an HCDR1 sequence and/or an HCDR2 sequence. In some embodiments, the HCDR3 sequence comprises an amino acid sequence selected from the group consisting of SEQ ID NOs: 17, 23, 29, 35, 41, 47, and 53; and/or, the HCDR2 sequence comprises an amino acid sequence selected from the group consisting of SEQ ID NOs: 16, 22, 28, 34, 40, 46, and 52; and/or, the HCDR1 sequence comprises an amino acid sequence selected from the group consisting of SEQ ID NOs: 15, 21, 27, 33, 39, 45, and 51.

In some embodiments, the antibody specifically binding to human MASP-2 or the antigen-binding fragment thereof further comprises a light chain variable region, wherein the light chain variable region comprises an LCDR1 sequence, an LCDR2 sequence, and/or an LCDR3 sequence. In some embodiments, the LCDR1 sequence comprises an amino acid sequence selected from the group consisting of SEQ ID NOs: 18, 24, 30, 36, 42, 48, and 54. And/or, the LCDR2 sequence comprises an amino acid sequence selected from the group consisting of SEQ ID NOs: 19, 25, 31, 37, 43, 49, and 55. And/or, the LCDR3 sequence comprises an amino acid sequence selected from the group consisting of SEQ ID NOs: 20, 26, 32, 38, 44, 50, and 56.

In some embodiments, the antibody is a monoclonal antibody; the antigen-binding fragment is selected from the group consisting of an Fab fragment, an Fab' fragment, an F(ab')2 fragment, an Fv fragment, an scFv fragment, an Fd fragment, and a single domain antibody.

The antibody specifically binding to human MASP-2 or the antigen-binding fragment thereof of the present disclosure comprises at least one CDR region, and the CDR region is selected from the following sequences or mutated sequences thereof or amino acid sequences having 90% sequence identity therewith: antibody heavy chain variable region (HCDR region): SEQ ID NOs: 15, 16, 17, 21, 22, 23, 27, 28, 29, 33, 34, 35, 39, 40, 41, 45, 46, 47, 51, 52, and 53; antibody light chain variable region (LCDR region): SEQ ID NOs: 18, 19, 20, 24, 25, 26, 30, 31, 32, 36, 37, 38, 42, 43, 44, 48, 49, 50, 54, 55, and 56.

In a preferred embodiment of the present disclosure, the antibody or the antigen-binding fragment thereof is a murine antibody or a fragment thereof. The light chain variable region of the murine antibody comprises an amino acid sequence selected from the group consisting of SEQ ID NOs: 2, 4, 6, 8, 10, 12, and 14, or an amino acid sequence having at least 95% homology therewith; the heavy chain variable region comprises an amino acid sequence selected from the group consisting of SEQ ID NOs: 1, 3, 5, 7, 9, 11, and 13, or an amino acid sequence having at least 95% homology therewith.

In a preferred embodiment of the present disclosure, there is provided the murine antibody or the fragment thereof as described above, which further comprises a heavy chain constant region derived from murine IgG1, IgG2, IgG3 or IgG4, or a variant thereof, and further comprises a light chain constant region derived from a murine c or A chain, or a variant thereof.

In a preferred embodiment of the present disclosure, there is provided the antibody specifically binding to human MASP-2 or the antigen-binding fragment thereof, which is a chimeric antibody or a humanized antibody or a fragment thereof.

In some embodiments, for the MASP-2 humanized antibody or the fragment thereof as described above, the humanized antibody comprises a combination of a heavy chain variable region sequence and a light chain variable region sequence selected from any one of the following sequences: a heavy chain variable region amino acid sequence of 100-Hu as shown in SEQ ID NO: 58, and a light chain variable region amino acid sequence of 100-Hu as shown in SEQ ID NO: 60; a heavy chain variable region amino acid sequence of 124-Hu as shown in SEQ ID NO: 64, and a light chain variable region amino acid sequence of 124-Hu as shown in SEQ ID NO: 66; a heavy chain variable region amino acid sequence of 126-Hu as shown in SEQ ID NO: 70, and a light chain variable region amino acid sequence of 126-Hu as shown in SEQ ID NO:72; a heavy chain variable region amino acid sequence of 136-Hu as shown in SEQ ID NO:76, and a light chain variable region amino acid sequence of 136-Hu as shown in SEQ ID NO:78.

In a preferred embodiment of the present disclosure, there is provided the MASP-2 humanized antibody or the fragment thereof as described above, which comprises a heavy chain constant region comprising human IgG1, IgG2, IgG3, or IgG4, or a variant thereof, and further comprises a light chain constant region comprising a human κ or λ chain, or a variant thereof. More preferably, it comprises a heavy chain constant region comprising human IgG4, or a variant thereof. The constant region can also be subject to modifications to change properties such as "YTE".

In a more preferred embodiment, the humanized antibody comprises a combination of a full-length heavy chain sequence and a full-length light chain sequence selected from any one of the following sequences: a full-length heavy chain amino acid sequence of 124-Hu as shown in SEQ ID NO: 67, and a full-length light chain amino acid sequence of 124-Hu as shown in SEQ ID NO: 68; a full-length heavy chain amino acid sequence of 126-Hu as shown in SEQ ID NO: 73, and a full-length light chain amino acid sequence of 126-Hu as shown in SEQ ID NO: 74.

According to a second aspect, the present disclosure provides a nucleotide molecule encoding the MASP-2 antibody or the antigen-binding fragment thereof as described above.

According to a third aspect, the present disclosure provides an expression vector containing the nucleotide molecule as described above.

In some embodiments, the expression vector is pTT5, pUC57, pDR1, pcDNA3.1(+), pDHFF, or pCHO 1.0, etc.

According to a fourth aspect, the present disclosure provides a host cell transformed with the expression vector. The host cell is HEK293, COS, CHO, NSO, sf9, sf21, DH5a, BL21(DE3), or TG1, etc., preferably a CHO cell.

According to a fifth aspect, the present disclosure provides a method for preparing the antibody specifically binding to human MASP-2 or the antigen-binding fragment thereof according to the first aspect, comprising the following steps:
a) culturing the host cell according to the fourth aspect under expression conditions that enable the host cell to produce the antibody or the antigen-binding fragment thereof, thereby expressing the antibody or the antigen-binding fragment thereof, and
b) separating and purifying the antibody or the antigen-binding fragment thereof expressed in the step a).

According to a sixth aspect, the present disclosure provides a pharmaceutical composition comprising the anti-human MASP-2 antibody or the antigen-binding fragment thereof according to the first aspect and a pharmaceutically acceptable carrier or excipient.

In some embodiments, the composition is used to treat MASP-2 related diseases.

According to a seventh aspect, the present disclosure provides a use of the anti-human MASP-2 antibody or the antigen-binding fragment thereof according to the first aspect, or the composition according to the sixth aspect for preventing or treating MASP-2 related diseases.

According to other aspects, the present disclosure provides a method for preventing or treating MASP-2 related diseases, comprising administering the antibody or the antigen-binding fragment thereof according to the first aspect, or the pharmaceutical composition according to the sixth aspect to an individual in need. The MASP-2 related diseases include: atypical hemolytic uremic syndrome, hematopoietic stem cell transplantation-associated thrombotic microangiopathy (HSCT-TMA), lupus nephritis, IgA nephropathy, etc.; wherein the disease is preferably IgA nephropathy.

DETAILED DESCRIPTION OF THE PREFERRED EMBODIMENT

Figure 1:
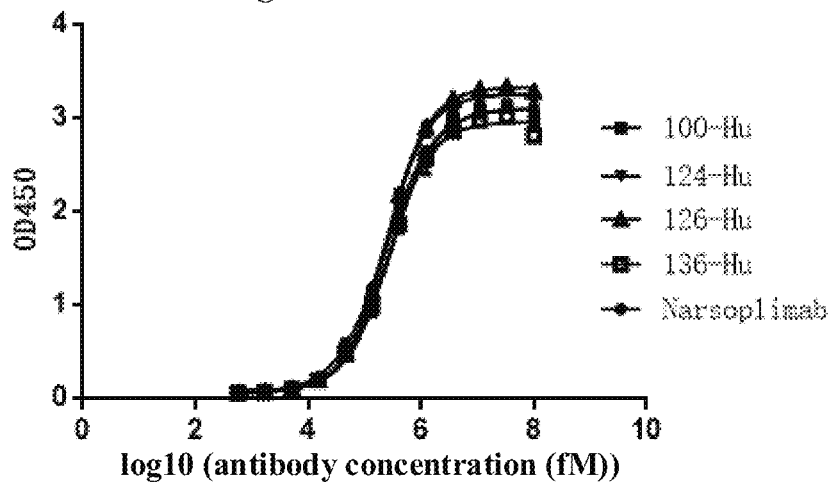
FIG. 1 shows the ELISA results of a humanized anti-human MASP-2 monoclonal antibody binding to human MASP-2.

The present disclosure provides a novel anti-human MASP-2 antibody specifically binding to human MASP-2 or an antigen-binding fragment thereof. In a preferred embodiment, the antibody or the antigen-binding fragment thereof of the present disclosure binds to human MASP-2 with high affinity and inhibits the enzymatic activity of MASP-2. The present disclosure further provides a polynucleotide encoding the antibody or the antigen-binding fragment thereof, a vector comprising the polynucleotide, a host cell comprising the polynucleotide or the vector, a method for preparing and purifying the antibody, and medical and biological applications of the antibody or the antigen-binding fragment thereof, such as preventing or treating MASP-2 related diseases. The present disclosure also covers a method for detecting MASP-2 and regulating the activity of MASP-2 by using the antibody or the antigen-binding fragment thereof.

To readily understand the present disclosure, some terms used herein are first defined.

As used herein, the term "antibody" refers to an immunoglobulin molecule comprising four polypeptide chains, namely, two heavy chains (H) and two light chains (L) interconnected by disulfide bonds, and a multimer thereof (e.g., IgM). Each heavy chain comprises a heavy chain variable region (VH) and a heavy chain constant region (CH). The heavy chain constant region comprises three domains: CH1, CH2 and CH3. Each light chain comprises a light chain variable region (VL) and a light chain constant region (CL). The light chain constant region comprises one domain (CL1). The VH and VL regions can be further subdivided into hypervariable regions called complementarity determining regions (CDRs), interspersed with conserved regions called framework regions (FRs).

As used herein, the term "antigen-binding fragment" of the antibody refers to a portion or segment of an intact antibody molecule that is responsible for binding an antigen. An antigen-binding domain may comprise a heavy chain variable region (VH), a light chain variable region (VL), or both. An antigen-binding fragment of the antibody can be prepared from the intact antibody molecule by using any suitable standard technology, including proteolytic digestion or recombinant genetic engineering technology, etc. Non-limiting examples of the antigen-binding fragment include: an Fab fragment; an F(ab')2 fragment; an Fd fragment; an Fv fragment; a single chain Fv (scFv) molecule; a single domain antibody; a dAb fragment, and a minimum recognition unit (e.g., separated CDR) consisting of amino acid residues simulating the hypervariable region of the antibody. The term "antigen-binding fragment" also includes other engineered molecules, such as bi-antibody, tri-antibody, tetra-antibody, and micro-antibody.

As used herein, the terms "heavy chain variable region (VH)" and "light chain variable region (VL)" refer to variable heavy chain and light chain regions of a single antibody, respectively, comprising FR1, FR2, FR3, and FR4, and CDR1, CDR2, and CDR3.

It is well known to those skilled in the art that complementarity determining regions (CDRs, typically CDR1, CDR2, and CDR3) are variable regions that have the greatest influence on affinity and specificity of antibodies. Two common definitions are available to CDR sequences of VH or VL, namely, definition by Kabat and definition by Chothia (see Kabat et al, "Sequences of Proteins of Immunological Interest", National Institutes of Health, Bethesda, Md. (1991); Al-Lazikani et al., JMB. 273:927-948 (1997); and Martin et al., PNAS. USA 86:9268-9272 (1989)). For a variable region sequence of a given antibody, CDR region sequences in VH and VL sequences can be determined based on the definitions by Kabat or Chothia. In an embodiment of the present disclosure, the CDR sequence is defined by Kabat. Herein, CDR1, CDR2, and CDR3 of the heavy chain variable region are referred to as HCDR1, HCDR2, and HCDR3, respectively; and CDR1, CDR2, and CDR3 of the light chain variable region are referred to as LCDR1, LCDR2, and LCDR3, respectively.

For the variable region sequence of the given antibody, a CDR region sequence in the variable region sequence can be analyzed in multiple ways, for example, the CDR region sequence can be determined by online software Abysis (http://www.abysis.org/).

As used herein, the term "specific binding" refers to a non-random binding reaction between two molecules, such as the binding of the antibody to an antigen epitope, such as the ability of the antibody to bind to a specific antigen with an affinity that is at least two times greater than its affinity for a nonspecific antigen. However, it should be understood that the antibody is capable of specifically binding to two or more antigens related to sequences of the antibody. For example, the antibody of the present disclosure can specifically bind to human and non-human (e.g., mice or non-human primates) MASP-2.

As used herein, the term "monoclonal antibody" refers to an antibody obtained from a substantially homogeneous antibody population, that is, the individual antibodies that make up the population are identical except for the possible naturally occurring mutations in a small number of individuals. The monoclonal antibody described herein particularly includes a "chimeric" antibody, in which a portion of the heavy chain and/or light chain is identical to or homologous with a corresponding sequence in an antibody from a specific species or belonging to a specific antibody class or subclass, while the rest of the heavy chain and/or light chain is identical to or homologous with a corresponding sequence in an antibody from another species or belonging to another antibody class or subclass; and the monoclonal antibody further comprises fragments of such antibody, as long as they exhibit the desired bioactivity (see U.S. Pat. No. 4,816,567; and Morrison et al, Proc. Natl. Acad. Sci. USA 81:6851-6855 (1984)).

As used herein, the term "homology" is defined as the percentage of identical residues in amino acid or nucleotide sequence variants after sequence alignment and introduction of gaps, which can be up to the maximum percentage if desired. Methods and computer programs for alignment are well known in the art. As used herein, "at least 90% homology" refers to any value from 90% to 100% homology, such as 91%, 93%, 95%, and 99%.

As used herein, the term "MASP-2 related disease" includes diseases and/or symptoms related to the enzymatic activity of MASP-2. Exemplary MASP-2 related diseases or disorders include atypical hemolytic uremic syndrome, hematopoietic stem cell transplantation-associated thrombotic microangiopathy (HSCT-TMA), lupus nephritis, IgA nephropathy, etc.

As used herein, the terms "half-life" and "serum half-life" refer to the time spent in reducing the serum concentration of an antigen-binding protein according to the present disclosure by 50% in vivo.

According to one aspect, the present disclosure provides an antibody specifically binding to human MASP-2 or an antigen-binding fragment thereof, comprising a heavy chain variable region and/or a light chain variable region. The CDR, VH, VL, heavy chain, and light chain amino acid sequences applicable to the antibody disclosed in the present disclosure are exemplarily listed in Tables 3 to 5 below. In some embodiments, the anti-human MASP-2 antibody or the antigen-binding fragment thereof comprises HCDR3, HCDR2, and/or HCDR1 sequences, which are independently selected from any one of the HCDR3, HCDR2, or HCDR1 sequences shown in Table 4. In some embodiments, the anti-human MASP-2 antibody of the present disclosure may further comprise a light chain CDR, which is independently selected from any one of the light chain LCDR1, LCDR2, or LCDR3 sequences shown in Table 4. For example, the anti-human MASP-2 antibody of the present disclosure may comprise any combination of the heavy chain variable regions and the light chain variable regions shown in Table 3.

In some embodiments, the HCDR3 of the antibody or antigen-binding fragment thereof disclosed herein is selected from the amino acid sequences as shown in SEQ ID NOs: 17, 23, 29, 35, 41, 47, and 53; the HCDR2 is selected from the amino acid sequences as shown in SEQ ID NOs: 16, 22, 28, 34, 40, 46, and 52; and/or, the HCDR1 is selected from the amino acid sequences as shown in SEQ ID NOs: 15, 21, 27, 33, 39, 45, and 51.

In a preferred embodiment, the HCDR3 is selected from the amino acid sequences as shown in SEQ ID NOs: 23, 41, 47, and 53; the HCDR2 is selected from the amino acid sequences as shown in SEQ ID NOs: 22, 40, 46, and 52; the HCDR1 is selected from the amino acid sequences as shown in SEQ ID NOs: 21, 39, 45, and 51. In a more preferred embodiment, the HCDR3 is selected from the amino acid sequences as shown in SEQ ID NOs: 41 and 47; the HCDR2 is selected from the amino acid sequences as shown in SEQ ID NOs: 40 and 46; the HCDR1 is selected from the amino acid sequences as shown in SEQ ID NOs: 39 and 45.

In some embodiments, the antibody heavy chain variable region disclosed herein comprises an amino acid sequence selected from the group consisting of SEQ ID NOs: 1, 3, 5, 7, 9, 11, 13, 58, 64, 70, and 76. In a preferred embodiment, the heavy chain variable region comprises an amino acid sequence selected from the group consisting of SEQ ID NOs: 58, 64, 70, and 76.

In some embodiments, the heavy chain variable region of the antibody disclosed herein comprises an amino acid sequence having at least 80%, 90%, 91%, 92%, 93%, 94%, 95%, 96%, 97%, 98%, 99% or more homology with the sequences as shown in SEQ ID NOs: 1, 3, 5, 7, 9, 11, 13, 58, 64, 70, and 76. In a preferred embodiment, the heavy chain variable region has more than 99% homology with the amino acid sequences as shown in SEQ ID NOs: 64 and 70.

The antibody or the antigen-binding fragment thereof disclosed herein may further comprise a light chain variable region in addition to the heavy chain variable region.

In some embodiments, the LCDR3 of the light chain variable region is selected from the amino acid sequences as shown in SEQ ID NOs: 20, 26, 32, 38, 44, 50, and 56; the LCDR2 is selected from the amino acid sequences as shown in SEQ ID NOs: 19, 25, 31, 37, 43, 49, and 55; and/or, the LCDR1 is selected from the amino acid sequences as shown in SEQ ID NOs: 18, 24, 30, 36, 42, 48, and 54.

In a preferred embodiment, the LCDR3 is selected from the amino acid sequences as shown in SEQ ID NOs: 26, 44, 50, and 56; the LCDR2 is selected from the amino acid sequences as shown in SEQ ID NOs: 25, 43, 49, and 55; the LCDR1 is selected from the amino acid sequences as shown in SEQ ID NOs: 24, 42, 48, and 54. In a more preferred embodiment, the LCDR3 is selected from the amino acid sequences as shown in SEQ ID NOs: 44 and 50; the LCDR2 is selected from the amino acid sequences as shown in SEQ ID NOs: 43 and 49; the LCDR1 is selected from the amino acid sequences as shown in SEQ ID NOs: 42 and 48.

In some embodiments, the light chain variable region of the antibody disclosed herein comprises an amino acid sequence having at least 80%, 90%, 91%, 92%, 93%, 94%, 95%, 96%, 97%, 98%, 99% or more homology with the sequences as shown in SEQ ID NOs: 2, 4, 6, 8, 10, 12, 14, 60, 66, 72, and 78. In a preferred embodiment, the heavy chain variable region has more than 99% homology with the amino acid sequences as shown in SEQ ID NOs: 66 and 72.

In some embodiments, at least one amino acid can be subjected to substitution, deletion, or addition on the corresponding specific amino acid sequences listed above in the heavy chain or heavy chain variable region, light chain or light chain variable region of the antibody disclosed herein, and a resulting variant still maintains the activity of binding human MASP-2.

In some embodiments, the number of amino acid substitutions, deletions, or additions is 1 to 30, preferably 1 to 20, and more preferably 1 to 10. In a preferred embodiment, the sequence variant differs from the original amino acid sequence by about 1, 2, 3, 4, 5, 6, 7, 8, 9, or 10 amino acid substitutions, deletions and/or additions. In a more preferred embodiment, the sequence variant differs from the original amino acid sequence by about 1, 2, 3, 4, or 5 amino acid substitutions, deletions, or additions. In a specific embodiment, the amino acid substitution is a conservative substitution.

In a preferred embodiment, the antibody disclosed herein is antibody 100-Hu, 124-Hu, 126-Hu, or 136-Hu. 100-Hu has a heavy chain variable region amino acid sequence as shown in SEQ ID NO: 58 and a light chain variable region amino acid sequence as shown in SEQ ID NO: 60, wherein the CDRs sequences are the same as that of antibody 100; 124-Hu has a heavy chain variable region amino acid sequence as shown in SEQ ID NO: 64 and a light chain variable region amino acid sequence as shown in SEQ ID NO: 66, wherein the CDRs sequences are the same as that of antibody 124; 126-Hu has a heavy chain variable region amino acid sequence as shown in SEQ ID NO: 70 and a light chain variable region amino acid sequence as shown in SEQ ID NO: 72, wherein the CDRs sequences are the same as that of antibody 126; 136-Hu has a heavy chain variable region amino acid sequence as shown in SEQ ID NO: 76 and a light chain variable region amino acid sequence as shown in SEQ ID NO: 78, wherein the CDRs sequences are the same as that of antibody 136.

In some embodiments, the antibody disclosed herein is a monoclonal antibody. In a specific preferred embodiment, the antibody disclosed herein is a humanized antibody.

The antibody or the antigen-binding fragment thereof disclosed herein is capable of specifically binding to human MASP-2. In a specific embodiment, the antibody or the antigen-binding fragment thereof specifically binds to human MASP-2 or monkey MASP-2.

In some embodiments, the antibody or the antigen-binding fragment thereof binds to human MASP-2 at a KD less than 1 nM. In a preferred embodiment, the antibody or the antigen-binding fragment thereof binds to MASP-2 (e.g., human MASP-2) at a KD less than 0.35 nM.

In some embodiments, the antibody or the antigen-binding fragment thereof disclosed herein is capable of inhibiting MASP-2-catalyzed C4 cleavage. In some embodiments, the antibody or the antigen-binding fragment thereof disclosed herein is capable of inhibiting C3 cleavage.

The inventors of the present disclosure have conducted a series of biological verification experiments on the anti-human MASP-2 monoclonal antibody disclosed herein, with the results showing that the antibody can bind to human MASP-2 well and has corresponding bioactivity.

Specifically, the inventors of the present disclosure have conducted affinity testing, MASP-2-catalyzed C4 cleavage, in vitro inhibition of C3 cleavage, and other experiments on the anti-human MASP-2 monoclonal antibody. The results show that the anti-human MASP-2 monoclonal antibody disclosed herein can bind to human MASP-2, inhibit the complement activation signal transduction of the lectin pathway, and contribute to the inhibition of the occurrence of inflammatory responses caused by excessive complement activation.

The present disclosure further provides a nucleotide molecule encoding the antibody or the antigen-binding fragment thereof disclosed herein, a vector comprising the polynucleotide, a host cell comprising the polynucleotide or the vector, and a method for preparing and purifying the antibody.

In some embodiments, the nucleotide molecule encoding the antibody or the antigen-binding fragment thereof is operably linked to a regulatory sequence that can be recognized by a host cell transformed with the vector.

In some embodiments, any suitable expression vector can be used in the present disclosure. For example, the expression vector may be one of pTT5, pUC57, pDR1, pcDNA3.1 (+), pDHFF, and pCHO 1.0. The expression vector may comprise a fusion DNA sequence linked with appropriate transcriptional and translational regulatory sequences.

In some embodiments, an available host cell is a cell comprising the expression vector, which may be a eukaryotic cell. For example, a mammalian or insect host cell culture system can be used for the expression of the antibody or the antigen-binding fragment thereof of the present disclosure. For example, HEK293 cells, COS, CHO, NSO, sf9, and sf21 are all applicable to the present disclosure. The host cell may also be a prokaryotic cell comprising the expression vector, such as DH5a, BL21 (DE3), or TG1.

In some embodiments, the method for preparing the anti-human MASP-2 monoclonal antibody disclosed herein comprises the following steps: culturing the host cell under expression conditions, thereby expressing the anti-human MASP-2 monoclonal antibody; and separating and purifying the expressed anti-human MASP-2 monoclonal antibody. A recombinant protein can be purified into a substantially homogeneous substance, such as a single band on SDS-PAGE, using the method.

In some embodiments, the anti-human MASP-2 antibody disclosed herein can be separated and purified by affinity chromatography. Based on properties of an affinity column used, the anti-human MASP-2 antibody binding to the affinity column can be eluted using a conventional method such as high-salt buffer and pH changing.

In some embodiments, the humanized anti-human MASP-2 monoclonal antibody disclosed herein is obtained by the following method: immunizing Balb/c mice with an MASP-2 antigen prepared in the laboratory, fusing mouse spleen cells with hybridoma cells with a higher titer after repeated immunization, and screening out hybridoma cell strains with the activity of inhibiting C4 cleavage. More specifically, through a large number of experiments by the inventors of the present disclosure, the MASP-2 antigen is firstly expressed respectively. On this basis, different adjuvants are mixed with the MASP-2 antigen to immunize mice, and then the mouse spleen cells are further fused with a hybridoma cell strain sp2/0. A positive cell strain is screened out from the fused hybridoma by using the MASP-2 antigen. After verifying that the positive cell strain inhibits C4 cleavage, a target cell strain is obtained. After humanization of a preferred target molecule, both light chain and heavy chain genes are cloned into a eukaryotic expression vector pCHO1.0. The expression vector is transfected into a CHO cell by lipofection. Positive cell clones are then screened with puromycin and methotrexate. The screened high-expression clones are expanded in a serum-free medium, and the humanized anti-human MASP-2 monoclonal antibody is separated or purified by a Protein A affinity column.

In some other embodiments, a conventional technique in the art, such as PCR mutagenesis, can be used to further change a murine parental antibody to produce chimeric or humanized forms or other variant forms of the antibody. The parental antibody of the present disclosure can be mutated in a domain such as an antigen complementarity determining region (CDR) to produce a variant antibody that can be screened for the presence of target properties such as binding affinity (lower KD), IC50, specificity, and priority binding. Preferably, the target properties in the variant antibody are improved properties compared to the parental antibody. Preferably, amino acids are substituted for the variant antibody, and at least 1, 2, 3, 4, 5, 6, 7, 8, 9, or 10 amino acid residues in molecules of the parental antibody are removed and different residues are inserted at corresponding positions.

The most interesting site for substitution mutagenesis is one or more CDR regions, but changes in a framework region (FR) are also considered. Conservative amino acid substitutions are preferred, and non-conservative amino acid changes can also be introduced, and the obtained variant antibody can be used to screen target properties.

In some embodiments, the serum half-life of the antibody is prolonged by transforming an Fc region of the antibody. Identified mutation sites that can improve the binding ability of human FcRn to antibodies mainly include T250Q, M252Y, S254T, T256E, V308P, M428L, N434A, and N434S. In this embodiment, the serum half-life of the antibody can be prolonged by mutation of amino acids at these sites.

The present disclosure provides a pharmaceutical composition comprising the antibody or the antigen-binding fragment thereof disclosed herein and a pharmaceutically acceptable carrier. The anti-human MASP-2 monoclonal antibody disclosed herein can be formulated into a pharmaceutical preparation together with the pharmaceutically acceptable carrier to achieve more stable efficacy. In some embodiments, these preparations can ensure the conformational integrity of the core amino acid sequence of the anti-human MASP-2 monoclonal antibody disclosed herein, while protecting multifunctional groups of proteins from degradation (including but not limited to aggregation, deamidation, or oxidation). In some embodiments, a liquid preparation can usually be kept stable at 2 to 8° C. for at least one year. In some embodiments, a lyophilized preparation is kept stable at 30° C. for at least six months.

In some embodiments, preparations of the anti-human MASP-2 monoclonal antibody can be suspensions, water injections, lyophilized preparations, etc., commonly used in the pharmaceutical field, preferably water injections or lyophilized preparations. For a water injection or lyophilized preparation of the anti-human MASP-2 monoclonal antibody disclosed herein, pharmaceutically acceptable excipients include, but are not limited to, surfactants, solution stabilizers, isotonic regulators, and buffers or combinations thereof. In some embodiments, the surfactants include, but are not limited to, nonionic surfactants such as polyoxyethylene sorbitan fatty acid ester (Tween 20 or 80), Poloxamer (e.g., Poloxamer 188), Triton, sodium dodecyl sulfate (SDS), sodium lauryl sulfate, tetradecyl, linoleoyl or octadecyl sarcosine, Pluronics, and MONAQUAT™, which should be added in such an amount that can minimize granulation trend of the anti-human MASP-2 monoclonal antibody. In some embodiments, the solution stabilizers include, but are not limited to, one or a combination of: saccharides, such as reducing saccharides and non-reducing saccharides; amino acids, such as monosodium glutamate or histidine; alcohols, such as triols, higher sugar alcohols, propylene glycol, and polyethylene glycol. The solution stabilizers should be added in such an amount that the final formed preparation keeps stable within the time considered stable by those skilled in the art. The isotonic regulators include, but are not limited to, sodium chloride, mannitol, or a combination thereof. The buffers include, but are not limited to, Tris, histidine buffer, phosphate buffered saline, or a combination thereof.

The present disclosure further provides a method for preventing or treating MASP-2 related diseases, comprising administering an anti-human MASP-2 antibody or a composition comprising the anti-human MASP-2 antibody to an individual.

The present disclosure further provides a use of the anti-human MASP-2 antibody or the composition comprising the anti-human MASP-2 antibody in the manufacture of a medicament for preventing or treating MASP-2 related diseases or symptoms. In some embodiments, the MASP-2 related disease or symptom is a complement activation-mediated disease.

In some embodiments, the MASP-2 related diseases include, but are not limited to, atypical hemolytic uremic syndrome, hematopoietic stem cell transplantation-associated thrombotic microangiopathy (HSCT-TMA), lupus nephritis, IgA nephropathy, etc.

When the anti-human MASP-2 monoclonal antibody and the composition thereof disclosed herein are administered to animals including humans, the dosage varies depending on age and weight of the patient, characteristics and severity of the disease, and route of administration. With reference to the results and comprehensive situations of animal experiments, the total dosage should not exceed a certain range.

The dosage and frequency of administration of the antibody or the composition thereof may vary depending on prevention or treatment of diseases. In a preventive application, a composition comprising the antibody of the present disclosure or a mixture thereof is administered to a patient who has not been in a disease state yet to enhance resistance of the patient in an amount defined as a "preventive effective dose". In this use, the specific dose depends on health and systemic immunity of the patient. A relatively low dose is usually administered at a relatively infrequent interval over a long period of time. In a therapeutic application, it is sometimes necessary to administer a relatively high dose at a relatively short interval until disease progression slows or stops, and preferably until the patient shows partial or complete improvement in disease symptoms. Thereafter, a preventive regimen can be administered to the patient. Those of ordinary skill in the art can easily master the specific dose and frequency based on actual needs.

In the specification and claims, the words "including", "comprising", and "containing" mean "including, but not limited to", and are not intended to exclude other parts, additives, components, or steps.

It should be understood that the features, characteristics, components, or steps described in specific aspects, embodiments, or examples of the present disclosure are applicable to any other aspects, embodiments, or examples described herein, unless there is a contradiction.

The above disclosure generally describes the present disclosure. The following specific examples are to further illustrate the present disclosure, and should not be construed as limiting the present disclosure. The examples do not include a detailed description of conventional methods, which are well known to those of ordinary skill in the art, and have been described in many publications, such as Molecular Cloning Manual, and Antibody Technology Laboratory Manual published by Cold Spring Harbor. Reagents without indication of sources are conventional reagents.

EXAMPLES

Example 1: Preparation of Soluble Human MASP-2-CCS Protein, Cynomolgus Monkey MASP-2-CCS Protein, and Reference Antibody Narsoplimab The human MASP-2-CCS antigen sequence was derived from UniProt (O00187). Codon optimization was carried out based on codon bias of *Homo sapiens*, and gene synthesis of amino acids at position 1 to 686 from N-terminus was performed. The sequence was subcloned into a pUC57 vector to obtain pUC57-hMASP-2. The monohFc fragment (Gly119-Gly329 of IGHG1, P01857, S247N/Y290N/K292T) and a Flag tag (DYKDDDDK) were inserted into the N-terminus of an hMASP-2-CCS fragment (Tyr293-Phe686, O00187) and an hMASP-2A-CCS fragment (Tyr293-Phe686, S633A, O00187) respectively by PCR, and constructed on a pTT5 expression vector (stored in the laboratory) to obtain expression vectors of Fc-hMASP-2-CCS, Flag-hMASP-2-CCS, Fc-hMASP-2A-CCS, and Flag-hMASP-2A-CCS. After the construction was completed, the vectors were sequenced, and the clones with completely correct sequences were selected for plasmid mass extraction for cell transfection.

The cynomolgus monkey MASP-2 sequence was derived from UniProt (F6SW75). The amino acids at positions 293 to 686 from N-terminus were subjected to codon optimization and gene synthesis based on codon bias of *Homo sapiens*. After adding a monohFc tag before the optimized sequence, the sequence was cloned into the pTT5 vector to obtain an expression vector of Fc-cyno-MASP-2-CCS, followed by plasmid mass extraction for cell transient transfection.

The plasmid was transfected into HEK293E cell line by PEI method. After cells were cultured in Freestyle293 medium (purchased from Gibco) containing 3 mM valproic acid for 5 days, a target protein was purified from the cell culture supernatant by Protein A affinity chromatography column (purchased from GE) or Flag affinity chromatography (purchased from Sigma). The protein was quantified by bicinchoninic acid (BCA) method, and the purified protein was used for the following mouse immunization and further analysis and research.

The amino acid sequence of Narsoplimab (IgG4, λ) was from the IMGT database. A nucleotide sequence was synthesized after codon optimization based on *Homo sapiens*, and cloned into the pTT5 expression vector to obtain pTT5 (Narsoplimab-HC) and pTT5 (Narsoplimab-LC). Both vectors were transiently transfected into the HEK293E cell line. Cells were cultured in Freestyle293 medium containing 3 mM valproic acid for 5 days, and then Narsoplimab antibody protein was purified from the cell culture supernatant by Protein A affinity chromatography column (purchased from GE).

Example 2: Production of Anti-Human MASP-2 Monoclonal Antibody

Anti-human MASP-2 monoclonal antibody was obtained by immunizing mice. The two antigens, Fc-hMASP-2-CCS and Fc-hMASP-2A-CCS at 100 μg/mouse were diluted with saline to 75 μL and mixed with an equal volume of Freund's complete adjuvant. After complete ultrasonic emulsification, 4 to 5 weeks old Balb/c mice (purchased from Shanghai Lingchang Biotechnology Co., Ltd, animal production license number: SCXK (Shanghai) 2013-0018) were injected subcutaneously at multiple sites. Three weeks later, the proteins at 50 μg/mouse were also diluted to 75 μL and mixed with an equal volume of Freund's incomplete adjuvant. After complete ultrasonic emulsification, mice were injected subcutaneously at multiple sites, and the immunization was repeated two weeks later. One week after the third immunization, tails of all mice were cut off to collect blood for serum separation, and the serum antibody titer was tested by ELISA coated with the Fc-hMASP-2-CCS and Fc-hMASP-2A-CCS antigens. For mice with a serum antibody titer greater than 10,000, a booster immunization was carried out one week after blood collection: tail vein injection of 10 μg antigen/100 μL saline/mouse.

The titer was tested by ELISA: an ELISA plate was coated with the Fc-hMASP-2A-CCS or Fc-hMASP-2-CCS antigen at a concentration of 1 μg/mL, 100 μL per well, and coated overnight at 4° C. The plate was washed twice with PBST (PBS containing 0.5% Tween-20) and then pat-dried. Each well was blocked with 200 μL of coating solution containing 1% BSA, blocked at room temperature for 4 hours, pat-dried, and stored in a refrigerator at -20° C. for use. During testing, 100 μL of mouse serum at different concentrations was added to each well of the ELISA plate, with two replicate wells for each concentration, and the plate was incubated at room temperature for 1.5 hours. The plate was washed three times with PBST and then pat-dried. 100 μL of HRP-labeled rabbit anti-mouse Ig antibody (purchased from Sigma) diluted with PBST by 1:10000 was added, and the plate was incubated at room temperature for 1 hour. The plate was washed three times with PBST and then pat-dried. 100 μL of chromogenic solution was added to each well (ELISA chromogenic solution A was mixed with chromogenic solution B at a volume ratio of 1:1 before use) for a chromogenic reaction, and then 100 μL of 2 M $H_2SO_4$ stopping solution was added to each well to terminate the reaction. The OD value of each well was immediately measured at 450 nm with a microplate reader (Molecular Device).

Example 3: Fusion and Screening of Hybridoma

Sp2/0 hybridoma cells (from the Cell Bank of the Committee on Type Culture Collection of Chinese Academy of Sciences, with an accession number of TCM-18) were cultured in a 5% $CO_2$ incubator at 37° C., and the medium was changed one day before fusion. Three days after booster immunization, spleen cells were collected from mice for fusion. A fusion and screening method was as follows: Mouse spleen was ground and washed. Spleen cells were then counted and mixed with sp2/0 cells at a ratio of 2:1. The mixture was centrifuged at 1000 rpm for 7 minutes. The supernatant was washed off. 1 mL of PEG (1450) was added within 1 minute, and shaken gently for 90 seconds. 5 mL of serum-free DMEM medium was added within 2.5 minutes, and then another 5 mL of serum-free medium was added at one time to terminate the reaction. The mixture was allowed to stand for 5 minutes, and centrifuged at 1280 rpm for 8 minutes. With 2 million sp2/0 cells in a 96-well plate, the cells were uniformly inoculated into the 96-well plate at 200 μL per well. An HAT medium containing hypoxanthine (H), aminopterin (A), and thymidine (T) was first used for screening, then half of the medium was changed every 3 to 4 days, and an HT medium was used on day 10. Ten days later, when hybridoma cells covered more than 10% of the bottom of the 96-well plate, the supernatant was tested by ELISA with an ELISA plate coated with the Fc-hMASP-2A-CCS antigen. The ELISA method was the same as that described in Example 2. Positive hybridomas were selected and cloned into a 24-well plate for expansion. The expanded hybridomas were subcloned by limiting dilution to obtain hybridoma strains stably expressing the target antibody, and then a cell bank was built with preserved hybridoma strains.

Example 4: Inhibition of Hybridoma Supernatant on MASP-2-Catalyzed C4 Cleavage C4 cleavage is catalyzed by MASP-2. C4 is cleaved into two parts, C4a and C4b, in the presence of MASP-2. In this catalytic system, detection of C4b concentration using an anti-C4b specific antibody will enable evaluation of the activity of MASP-2.

Hybridoma cell culture medium was exchanged with SFM medium (purchased from Gibco) containing 2.5% inactivated FBS one day in advance, then DMEM was exchanged for SFM, and the culture supernatant was taken and mixed with 1×TBS at a ratio of 1:1 for C4 detection as follows: 1) A 96-well plate was coated with mannose (100 μL/well, 10 μg/mL; Sigma), allowed to stand overnight at 4° C., washed with TBS, blocked with blocking solution at 37° C. for 2 hours, pat-dried, and stored in a refrigerator at -20° C. for use; 2) human serum (MILLIPORE, S1-100 mL) was diluted to 4% with binding buffer (TBS, 1 M NaCl, 10 mM $CaCl_2$), 0.05% Triton X-100, pH 7.4), added to the 96-well plate coated with mannose, the plate was allowed to stand overnight at 4° C., and washed three times with washing buffer (TBS, 5 mM $CaCl_2$); 0.05% Tween 20, pH 7.4); 3) hybridoma supernatant was added to GVB++ buffer (GVB buffer, 5 mM $CaCl_2$), 2.5 mM $MgCl_2$; 1:3.5 dilution; 50 μL/well), the plate was allowed to stand at room temperature for 0.5 hours, added with human C4 component (Calbiochem; GVB++ buffer; 50 μL/well, 3 μg/mL), reacted at 37° C. for 1.5 hours, and placed on ice for 10 minutes to terminate the enzyme reaction; 4) the 96-well plate was washed three times with PBST, added with the anti-C4b antibody (Assay Pro; 1:4000), allowed to stand at 37° C. for 1 hour, washed, added with HRP-labeled antibody (purchased from BD Pharmingen) diluted with PBST by 1:5000, incubated at room temperature for 1 hour, washed three times with PBST, and pat-dried. 100 μL of chromogenic solution was added to each well (ELISA chromogenic solution A was mixed with chromogenic solution B at a volume ratio of 1:1 before use) for a chromogenic reaction, and then 100 μL of 2 M $H_2SO_4$ stopping solution was added to each well to terminate the reaction. The OD value of each well was immediately measured at 450 nm with a microplate reader (Molecular Device), and the data were analyzed using Graphpad Prism software.

Example 5: Binding of Murine Anti-Human MASP-2 Monoclonal Antibody to Human and Cynomolgus Monkey MASP-2

Preferred murine antibodies were obtained according to the screening method described above. Murine anti-human MASP-2 monoclonal antibodies were purified by a Protein G affinity chromatography column, and then quantified by BCA method. The EC50 of anti-human MASP-2 monoclonal antibody binding to Fc-hMASP-2A-CCS or Fc-cyno-MASP-2-CCS was tested by ELISA. The testing method can refer to Example 2. A 96-well ELISA plate was coated with 1 μg/mL of Fc-hMASP-2A-CCS or Fc-cyno-MASP-2-CCS, and then added with murine anti-human MASP-2 monoclonal antibodies at different concentrations for testing. The EC50 data of some of the preferred antibodies were listed in Table 1. These antibodies had high affinity for human MASP-2, with EC50 ranging from 140 to 190 pM. Some of the antibodies, such as 60, 120, and 124, could also recognize cynomolgus monkey MASP-2 at the same time.

TABLE 1

Binding of exemplary murine anti-human MASP-2 monoclonal antibody to human and cynomolgus monkey MASP-2-CCS

| Murine antibody number | Human MASP-2 EC50 (pM) | Cynomolgus monkey MASP-2 EC50 (pM) |
|---|---|---|
| 60 | 148.800 | 95.956 |
| 100 | 172.642 | No binding |
| 115 | 150.879 | No binding |
| 120 | 159.699 | 159.554 |
| 124 | 182.204 | 178.647 |
| 126 | 160.620 | No binding |
| 136 | 143.477 | No binding |

Example 6: Inhibition of Murine Anti-Human MASP-2 Monoclonal Antibody on MASP-2-Catalyzed C4 Cleavage Purified murine anti-human MASP-2 monoclonal antibody was obtained according to the method in Example 5. The inhibitory effect of the above antibodies on MASP-2-catalyzed C4 cleavage was analyzed with reference to the method in Example 4, with Narsoplimab as the reference antibody. The IC50 data of some of the preferred antibodies were listed in Table 2. The experimental results showed that the preferred antibodies significantly inhibited the ability of MASP-2 to catalyze C4 cleavage, with IC50 ranging from 75 to 280 pM. The vast majority of the preferred antibodies had significantly higher inhibitory activity than the reference antibody Narsoplimab.

TABLE 2

Inhibition of exemplary murine anti-human MASP-2 monoclonal antibody on MASP-2-catalyzed C4 cleavage

| Murine antibody number | IC50 (pM) |
|---|---|
| 60 | 160.670 |
| 100 | 238.436 |
| 115 | 82.573 |
| 120 | 275.255 |
| 124 | 149.804 |
| 126 | 77.400 |
| 136 | 75.683 |
| Narsoplimab | 286.676 |

Example 7: Determination of Variable Region Sequence of Murine Anti-Human MASP-2 Monoclonal Antibody Total RNA of each hybridoma cell strain was extracted by Trizol, and mRNA was reversely transcribed into cDNA by a reverse transcription kit (purchased from Takara). Light chain variable region and heavy chain variable region genes of murine anti-human MASP-2 monoclonal antibodies were obtained by PCR amplification with primers reported in the literature. PCR products were then cloned into a pGEM-T vector, and variable region gene sequences were sequenced and analyzed. Based on the results of various functional experiments and early druggability analysis, we finally selected 7 antibodies listed in Table 2 as leading antibodies, and sequenced to obtain nucleotide sequences of light and heavy chain variable regions. The transformed amino acid sequences were aligned and analyzed in GenBank, and all sequences were consistent with the characteristics of mouse IgG variable region genes. The variable region sequence information on each candidate antibody was shown in Table 3. Antibody 60 has a heavy chain variable region amino acid sequence as shown in SEQ ID NO: 1; and a light chain variable region amino acid sequence as shown in SEQ ID NO: 2. Antibody 100 has a heavy chain variable region amino acid sequence as shown in SEQ ID NO: 3; and a light chain variable region amino acid sequence as shown in SEQ ID NO: 4. Antibody 115 has a heavy chain variable region amino acid sequence as shown in SEQ ID NO: 5; and a light chain variable region amino acid sequence as shown in SEQ ID NO: 6. Antibody 120 has a heavy chain variable region amino acid sequence as shown in SEQ ID NO: 7; and a light chain variable region amino acid sequence as shown in SEQ ID NO: 8. Antibody 124 has a heavy chain variable region amino acid sequence as shown in SEQ ID NO: 9; and a light chain variable region amino acid sequence as shown in SEQ ID NO: 10. Antibody 126 has a heavy chain variable region amino acid sequence as shown in SEQ ID NO: 11; and a light chain variable region amino acid sequence as shown in SEQ ID NO: 12. Antibody 136 has a heavy chain variable region amino acid sequence as shown in SEQ ID NO: 13; and a light chain variable region amino acid sequence as shown in SEQ ID NO: 14. Amino acid sequences of light chain variable regions and heavy chain variable regions of murine anti-human MASP-2 monoclonal antibodies were analyzed based on Kabat rule, and three CDRs and four FRs were determined. Taking antibody 126 as an example, amino acid sequences of a heavy chain complementarity determining region of the antibody were HCDR1: SFGMH (SEQ ID NO: 45), HCDR2: YISSGSSSSFYVDTVKG (SEQ ID NO: 46), and HCDR3: GDRNFEV (SEQ ID NO: 47); and amino acid sequences of a light chain complementarity determining region of the antibody were LCDR1: RASQSVSSSRYSYMH (SEQ ID NO: 48), LCDR2: HASNLES (SEQ ID NO: 49), and LCDR3: QQSWEVPWT (SEQ ID NO: 50). The CDR sequence information on each candidate antibody was shown in Table 4.

TABLE 3

Amino acid sequences of heavy and light chain variable regions of exemplary murine anti-human MASP-2 antibodies

| Murine antibody number | Heavy chain variable region amino acid sequence number (SEQ ID NO.) | Light chain variable region amino acid sequence number (SEQ ID NO.) |
|---|---|---|
| 60 | 1 | 2 |
| 100 | 3 | 4 |
| 115 | 5 | 6 |
| 120 | 7 | 8 |
| 124 | 9 | 10 |
| 126 | 11 | 12 |
| 136 | 13 | 14 |

TABLE 4

Amino acid sequences of heavy and light chain CDRs of exemplary murine anti-human MASP-2 antibodies

| Murine antibody number | Sequence number corresponding to HCDR1 (SEQ ID NO.) | Sequence number corresponding to HCDR2 (SEQ ID NO.) | Sequence number corresponding to HCDR3 (SEQ ID NO.) | Sequence number corresponding to LCDR1 (SEQ ID NO.) | Sequence number corresponding to LCDR2 (SEQ ID NO.) | Sequence number corresponding to LCDR3 (SEQ ID NO.) |
|---|---|---|---|---|---|---|
| 60 | 15 | 16 | 17 | 18 | 19 | 20 |
| 100 | 21 | 22 | 23 | 24 | 25 | 26 |
| 115 | 27 | 28 | 29 | 30 | 31 | 32 |
| 120 | 33 | 34 | 35 | 36 | 37 | 38 |
| 124 | 39 | 40 | 41 | 42 | 43 | 44 |
| 126 | 45 | 46 | 47 | 48 | 49 | 50 |
| 136 | 51 | 52 | 53 | 54 | 55 | 56 |

Example 8: Humanization of Anti-Human MASP-2 Monoclonal Antibody

Based on the results of sequence analysis, antibodies 100, 124, 126, and 136 were selected to construct chimeric antibodies and humanized antibodies. The chimeric antibodies were constructed by intercepting heavy chain variable regions and light chain variable regions of murine antibodies, and connecting these regions with a heavy chain constant region of human IgG4 and a constant region of human K chain respectively by overlapping PCR.

Amino acid sequences of light chain variable regions and heavy chain variable regions of murine anti-human MASP-2 monoclonal antibodies were analyzed based on Kabat rule, and three CDRs and four FRs were determined. Taking antibody 126 as an example, based on the comparison of homology with human IgG Germline sequences at NCBI IgBlast, IGHV3-30*03 was selected as a heavy chain CDR grafting template, and the heavy chain CDR regions of the murine anti-human MASP-2 monoclonal antibody 126 were grafted into the framework regions of IGHV3-30*03 to construct a heavy chain CDR grafting antibody. Similarly, based on the comparison of homology with human IgG Germline sequences, IGKV1-39*01 was selected as a light chain CDR grafting template, and the light chain CDR regions of the murine anti-human MASP-2 monoclonal antibody 126 were grafted into the framework regions of IGKV1-39*01 to construct a light chain CDR grafting antibody. The variable region gene sequences were optimized and synthesized by Sangon Biotech based on codon bias of *Homo sapiens*. The synthesized humanized variable region sequence was linked to a human IgG4 constant region. At the same time, on this basis, some amino acid sites in the framework region were subjected to back mutation. During the back mutation, amino acid sequences were encoded by Kabat, and locations of the sites were indicated by Kabat codes. After a series of back mutation screening, preferably, for the light chain variable region sequence, Y at position 36 of a Kabat code was reverted to murine F. There was no back mutation in the heavy chain variable region. This antibody was defined as a humanized antibody (126-Humanization, 126-Hu) of antibody 126.

Based on the same principle described above, the other three antibodies were also humanized, and the sequence information on the humanized antibodies was shown in Table 5. Transiently expressed vectors of humanized heavy chains and light chains were constructed by a pTT5 vector, then a combination of the above heavy chains and light chains was subject to transient transfection with a HEK293 system, and antibodies were expressed. HEK293 cells were cultured in Free Style 293 Expression Medium (purchased from Gibco). Plasmids were transfected into the cells by PEI transfection. Five days later, a cell supernatant was collected and purified by Protein A to obtain a humanized antibody.

Finally, a humanized heavy chain variable region of antibody 100 has a gene sequence with a total length of 348 bp, encoding 116 amino acid residues, with a nucleotide sequence as shown in SEQ ID NO: 57 and an amino acid sequence as shown in SEQ ID NO: 58; and a humanized light chain variable region of antibody 100 has a gene sequence with a total length of 333 bp, encoding 111 amino acid residues, with a nucleotide sequence as shown in SEQ ID NO: 59 and an amino acid sequence as shown in SEQ ID NO: 60. After the heavy and light chain variable regions were linked to the constant region of human IgG4, a humanized 100-Hu heavy chain with 443 amino acids (with a sequence as shown in SEQ ID NO: 61) and a humanized 100-Hu light chain with 218 amino acids (with a sequence as shown in SEQ ID NO: 62) were finally obtained.

A humanized heavy chain variable region of antibody 124 has a gene sequence with a total length of 342 bp, encoding 114 amino acid residues, with a nucleotide sequence as shown in SEQ ID NO: 63 and an amino acid sequence as shown in SEQ ID NO: 64; and a humanized light chain variable region of antibody 124 has a gene sequence with a total length of 321 bp, encoding 107 amino acid residues, with a nucleotide sequence as shown in SEQ ID NO: 65 and an amino acid sequence as shown in SEQ ID NO: 66. After the heavy and light chain variable regions were linked to the constant region of human IgG4, a humanized 124-Hu heavy chain with 441 amino acids (with a sequence as shown in SEQ ID NO: 67) and a humanized 124-Hu light chain with 214 amino acids (with a sequence as shown in SEQ ID NO: 68) were finally obtained.

A humanized heavy chain variable region of antibody 126 has a gene sequence with a total length of 348 bp, encoding 116 amino acid residues, with a nucleotide sequence as shown in SEQ ID NO: 69 and an amino acid sequence as shown in SEQ ID NO: 70; and a humanized light chain variable region of antibody 126 has a gene sequence with a total length of 333 bp, encoding 111 amino acid residues, with a nucleotide sequence as shown in SEQ ID NO: 71 and an amino acid sequence as shown in SEQ ID NO: 72. After the heavy and light chain variable regions were linked to the constant region of human IgG4, a humanized 126-Hu heavy chain with 443 amino acids (with a sequence as shown in SEQ ID NO: 73) and a humanized 126-Hu light chain with 218 amino acids (with a sequence as shown in SEQ ID NO: 74) were finally obtained.

A humanized heavy chain variable region of antibody 136 has a gene sequence with a total length of 351 bp, encoding 117 amino acid residues, with a nucleotide sequence as shown in SEQ ID NO: 75 and an amino acid sequence as shown in SEQ ID NO: 76; and a humanized light chain variable region of antibody 136 has a gene sequence with a total length of 333 bp, encoding 111 amino acid residues, with a nucleotide sequence as shown in SEQ ID NO: 77 and an amino acid sequence as shown in SEQ ID NO: 78. After the heavy and light chain variable regions were linked to the constant region of human IgG4, a humanized 136-Hu heavy chain with 444 amino acids (with a sequence as shown in SEQ ID NO: 79) and a humanized 136-Hu light chain with 218 amino acids (with a sequence as shown in SEQ ID NO: 80) were finally obtained.

Figure 2:
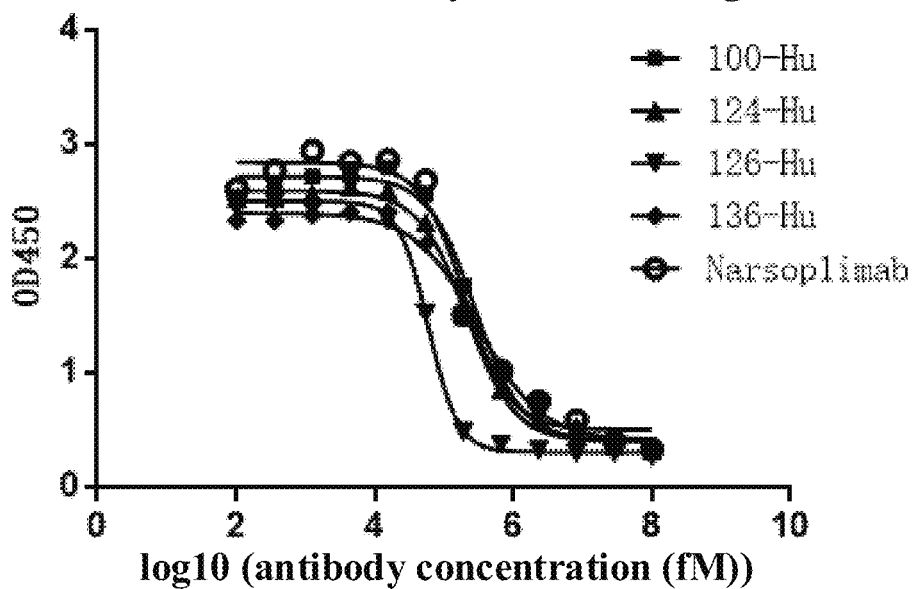
FIG. 2 shows the experimental results of inhibiting MASP-2-catalyzed C4 cleavage by a humanized anti-human MASP-2 monoclonal antibody in 4% human serum.

Example 9: Evaluation of In Vitro Activity of Humanized Anti-Human MASP-2 Monoclonal Antibody Humanized antibodies 100, 124, 126, and 136 were transiently expressed and purified. After quantification by BCA method, the affinity of each antibody for human MASP-2-CCS was detected according to Example 5. The experimental results were shown in FIG. 1 and Table 6. The inhibitory effect of each antibody on MASP-2-catalyzed C4 cleavage was investigated with reference to Example 4, and the experimental results were shown in FIG. 2 and Table 6.

The above experimental results showed that the affinity and in vitro bioactivity of the candidate humanized antibodies were basically the same as those of the murine antibody. The bioactivity of the 126-Hu antibody was significantly better than that of the reference antibody, and its ability to inhibit C4 cleavage in vitro was more than 3 times that of the reference antibody.

TABLE 6

In vitro activity of humanized MASP-2 antibody

| Humanized antibody | Human MASP-2 EC50 (pM) | C4 cleavage IC50 (pM) |
|---|---|---|
| 100-Hu | 296.979 | 280.715 |
| 124-Hu | 249.612 | 214.100 |
| 126-Hu | 246.343 | 59.831 |
| 136-Hu | 260.184 | 311.495 |
| Narsoplimab | 227.281 | 200.995 |

Example 10: Affinity of Humanized Anti-Human MASP-2 Antibody for MASP-2

The above four candidate humanized antibodies were expressed and purified, whose affinity was detected by Biacore T200 (GE healthcare), with the reference antibody Narsoplimab as a control. The specific experimental method was as follows: a Protein-A CMS sensor chip (GE healthcare) was used, with FC1 (Flow cell 1) as a reference channel, and FC2 (Flow cell 2) as a sample channel. Humanized antibodies or control antibody were captured in the FC2 channel, and then MASP-2-CCS-Flag at different concentrations was injected. Cycling conditions were as follows: an analyte was injected into all channels of FCs at a rate of 30 μL/min for 4 minutes, with a dissociation time of 20 minutes, and Glycine pH 1.5 (GE healthcare) was injected at a rate of 50 μL/min for 30 seconds for surface regeneration. Signal differences between captured and non-captured antibodies and affinity for interaction were then calculated by Biacore T200 Evaluation Software Ver 1.0. As shown in Table 7, the affinity of the humanized candidate antibodies for MASP-2-CCS was significantly higher than that of the reference antibody Narsoplimab. The affinity of 124-Hu was 25 times that of the reference antibody, and the affinity of 126-Hu was 60 times that of the reference antibody. 124-Hu could bind to cynomolgus monkey MASP-2 with an affinity of 0.245 nM.

TABLE 5

Sequence information on humanized antibodies

| Humanized antibody | Sequence number corresponding to nucleotide of heavy chain variable region (SEQ ID NO.) | Sequence number corresponding to amino acid of heavy chain variable region (SEQ ID NO.) | Sequence number corresponding to nucleotide of light chain variable region (SEQ ID NO.) | Sequence number corresponding to amino acid of light chain variable region (SEQ ID NO.) | Sequence number corresponding to humanized heavy chain amino acid (SEQ ID NO.) | Sequence number corresponding to humanized light chain amino acid (SEQ ID NO.) |
|---|---|---|---|---|---|---|
| 100-Hu | 57 | 58 | 59 | 60 | 61 | 62 |
| 124-Hu | 63 | 64 | 65 | 66 | 67 | 68 |
| 126-Hu | 69 | 70 | 71 | 72 | 73 | 74 |
| 136-Hu | 75 | 76 | 77 | 78 | 79 | 80 |

TABLE 7

Affinity of humanized antibody for human MASP-2

| Antibody | Ka (1/Ms) | Kd (1/s) | KD (nM) |
|---|---|---|---|
| 100-Hu | $4.285 \times 10^5$ | $2.985 \times 10^{-4}$ | 0.701 |
| 124-Hu | $1.661 \times 10^6$ | $5.819 \times 10^{-4}$ | 0.350 |
| 126-Hu | $4.281 \times 10^5$ | $6.329 \times 10^{-5}$ | 0.148 |
| 136-Hu | $5.900 \times 10^5$ | $5.889 \times 10^{-4}$ | 0.998 |
| Narsoplimab | $1.924 \times 10^6$ | $1.700 \times 10^{-2}$ | 8.834 |

Example 11: Inhibition of Humanized Anti-Human MASP-2 Antibody on Production of C3b After C4b was produced by MASP-2-catalyzed C4 cleavage, C4b bound to C2a to form C3 convertase, which cleaved C3 into C3b and C3a. Detection of C3b concentration in the reaction system using an anti-C3b specific antibody will enable characterization of the activity of MASP-2.

Figure 3:
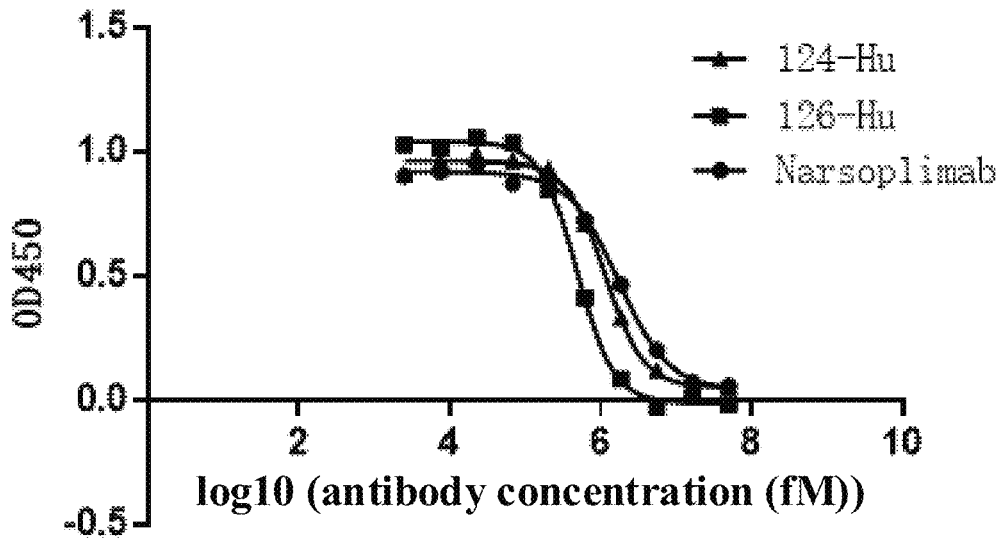
FIG. 3 shows the experimental results of inhibiting MASP-2-mediated C3b production by a humanized anti-human MASP-2 monoclonal antibody.

The experimental operation of anti-human MASP-2 monoclonal antibody to inhibit MASP-2-mediated C3b production was as follows: 1) A 96-well plate was coated with mannose (100 μL/well, 10 μg/mL; Sigma), allowed to stand overnight at 4° C., washed with TBS, blocked with blocking solution at 37° C. for 2 hours, washed three times with TBS, and then rinsed once with GVB++ buffer (150 μL/well, GVB, 5 mM $CaCl_2$), 2.5 mM $MgCl_2$); 2) C1q-removed human serum (Chemicon) was diluted to 4% with GVB++ buffer, premixed with 3.5-fold serially diluted candidate antibody, and the mixture was allowed to stand at 4° C. for 1 hour; 3) the mixture of 4% serum and antibody was added to the 96-well plate coated with mannose (100 μL/well) on ice, the plate was incubated at 37° C. for 1.5 hours, placed on ice for 10 minutes to terminate the reaction, and then washed three times with PBST; 4) the plate was added with the anti-C3c antibody (1:8000; Dako), incubated at 37° C. for 1 hour, washed three times, added with anti-rabbit IgG-HRP antibody (1:5000; Invitrogen), incubated at 37° C. for 1 hour, and then washed three times; 5) 100 μL of chromogenic solution was added to each well (ELISA chromogenic solution A was mixed with chromogenic solution B at a volume ratio of 1:1 before use) for a chromogenic reaction, and then 100 μL of 2 M $H_2SO_4$ stopping solution was added to each well to terminate the reaction. The OD value of each well was immediately measured at 450 nm with a microplate reader (Molecular Device). The results of data analysis using Graphpad Prism software were shown in FIG. 3, in which the IC50 of 124-Hu, 126-Hu, and Narsoplimab were 1.143 nM, 0.494 nM, and 1.735 nM, respectively. The bioactivity of the 126-Hu antibody was significantly better than that of the reference antibody, and its ability to inhibit C3b production in vitro was about 3.5 times that of the reference antibody.

Figure 4:
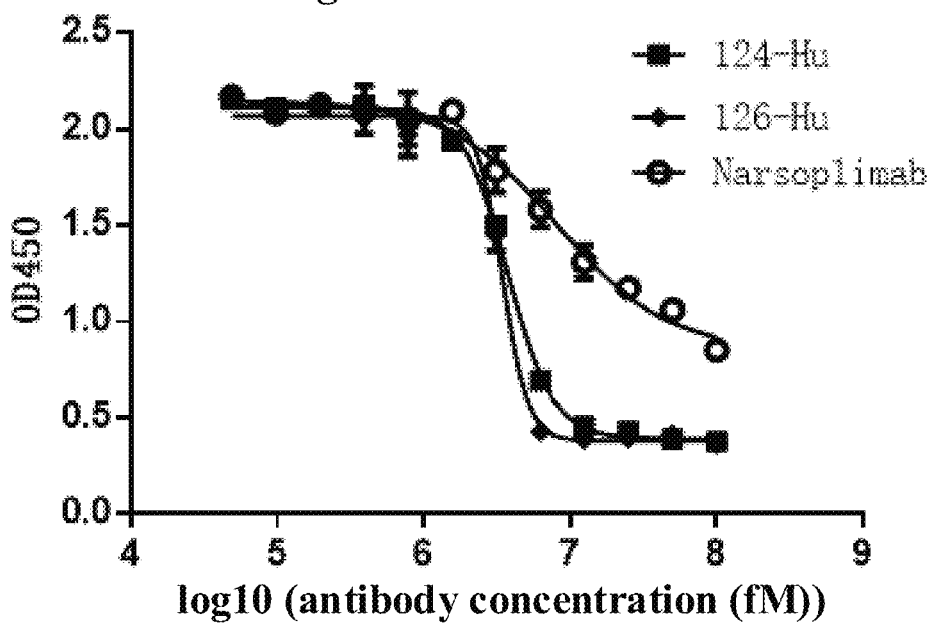
FIG. 4 shows the experimental results of inhibiting MASP-2-catalyzed C4 cleavage by a humanized anti-human MASP-2 antibody in 90% human serum.
Figure 5:
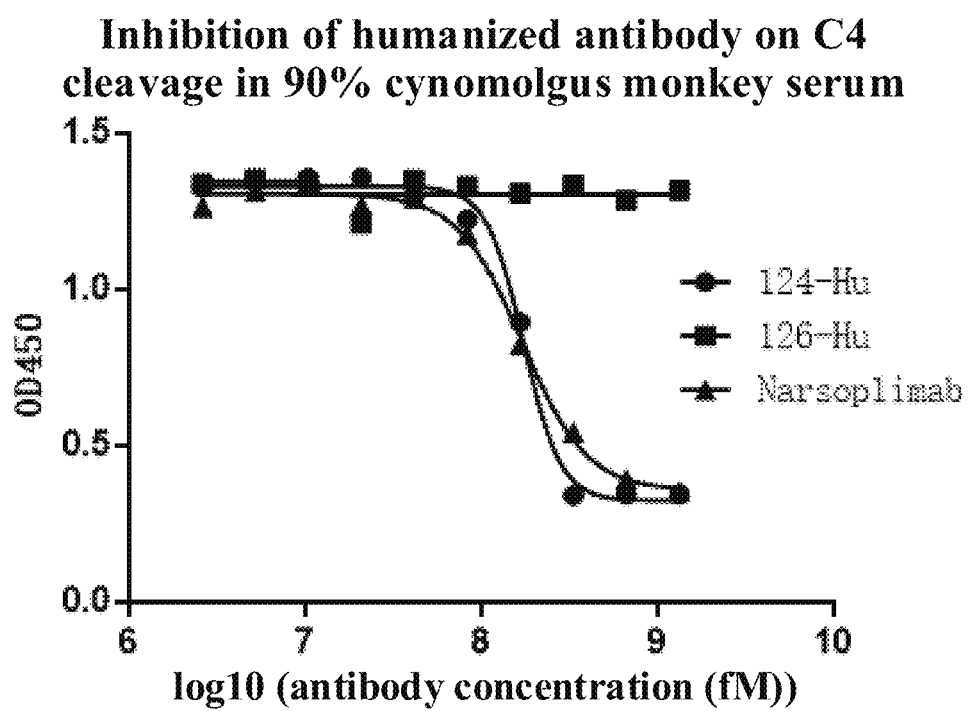
FIG. 5 shows the experimental results of inhibiting MASP-2-catalyzed C4 cleavage by a humanized anti-human MASP-2 antibody in 90% cynomolgus monkey serum.

Example 12: Assay of Inhibition of MASP-2-Catalyzed C4 Cleavage by Humanized Anti-Human MASP-2 Antibody in 90% Serum To simulate the in vivo environment, the serum concentration was increased to 90% serum in the reaction system. The experimental steps of antibody to inhibit C4 cleavage were as follows: 1) A 96-well plate was coated with mannose (100 μL/well, 10 μg/mL; Sigma), allowed to stand overnight at 4° C., washed with TBS, blocked with blocking solution at 37° C. for 2 hours, washed three times with TBS, and then rinsed once with GVB++ buffer (150 μL/well, GVB, 5 mM $CaCl_2$), 2.5 mM $MgCl_2$); 2) the candidate antibody was 3.5-fold serially diluted with GVB++ buffer, and a mixture of 90% v/v human or cynomolgus monkey serum and 10% v/v antibody was incubated at 4° C. for 1 hour; 3) the above premix was added to the 96-well plate coated with mannose, the plate was incubated at 37° C. for 1.5 hours, placed on ice for 10 minutes to terminate the reaction, and then washed three times with PBST; 4) the 96-well plate was washed three times with PBST, added with the anti-C4b antibody (Assay Pro; 1:4000), allowed to stand at 37° C. for 1 hour, washed, added with HRP-labeled antibody (purchased from BD Pharmingen) diluted with PBST by 1:5000, incubated at room temperature for 1 hour, washed three times with PBST, and pat-dried. 100 μL of chromogenic solution was added to each well (ELISA chromogenic solution A was mixed with chromogenic solution B at a volume ratio of 1:1 before use) for a chromogenic reaction, and then 100 μL of 2 M $H_2SO_4$ stopping solution was added to each well to terminate the reaction. The OD value of each well was immediately measured at 450 nm with a microplate reader (Molecular Device). The results of experimental data analysis were detailed in FIG. 4 and FIG. 5. In the experiment of 90% human serum, the IC50 of 124-Hu, 126-Hu, and Narsoplimab were 3.750 nM, 3.457 nM, and 8.229 nM, respectively; in the experiment of 90% cynomolgus monkey serum, the IC50 of 124-Hu and Narsoplimab were 167.600 nM and 94.050 nM, respectively. The results showed that in 90% serum, the candidate antibodies also had strong inhibitory effect on C4 cleavage, and in 90% human serum, 124-Hu and 126-Hu had significantly higher C4 inhibitory activity than the reference antibody, with potentially better bioactivity in humans.

Conclusion: In affinity determination and analysis of various functional activities in vitro, the antibodies of the present disclosure show consistently stronger bioactivity than the control antibody Narsoplimab.

It can be understood that although the present disclosure is described in some form, the present disclosure is not limited to what is shown and described in the specification. It is obvious to those skilled in the art that various changes can be made to the embodiments and/or a feature or parameter without departing from the scope of the present disclosure. These changes are within the scope set forth by the present disclosure.

What is claimed is:

1. An antibody specifically binding to human MASP-2 or an antigen-binding fragment thereof, comprising a heavy chain variable region, wherein the heavy chain variable region comprises an HCDR3 sequence, an HCDR2 sequence and an HCDR1 sequence, wherein the HCDR3 sequence comprises an amino acid sequence as shown in SEQ IDS NO: 47; and, the HCDR2 sequence comprises an amino acid sequence as shown in SEQ ID NO: 46; and, the HCDR1 sequence comprises an amino acid sequence as shown in SEQ ID NO: 45;

and, the antibody or the antigen-binding fragment thereof further comprising a light chain variable region, wherein the light chain variable region comprises an LCDR1 sequence, an LCDR2 sequence, and an LCDR3 sequence, wherein the LCDR3 sequence comprises an amino acid sequence as shown in SEQ ID NO: 50; and, the LCDR2 sequence comprises an amino acid sequence as shown in SEQ ID NO: 49; and, the LCDR1 sequence comprises an amino acid sequence as shown in SEQ ID NO: 48.

2. The antibody or the antigen-binding fragment thereof according to claim 1, wherein the antibody or the antigen-binding fragment thereof is a murine antibody or an antigen-binding fragment thereof.

3. The antibody or the antigen-binding fragment thereof according to claim 2, wherein the murine antibody have a heavy chain variable region comprising an amino acid sequence as shown in SEQ ID NO: 11; wherein the murine antibody have a light chain variable region comprising an amino acid sequence as shown in SEQ ID NO: 12.

4. The antibody or the antigen-binding fragment thereof according to claim 1, wherein the antibody or the antigen-binding fragment thereof is humanized to obtain a humanized antibody or an antigen-binding fragment thereof.

5. The antibody or the antigen-binding fragment thereof according to claim 4, comprising a combination of a heavy chain variable region sequence as shown in SEQ ID NO: 70 and a light chain variable region sequence as shown in SEQ ID NO: 72.

6. The antibody or the antigen-binding fragment thereof according to claim 1, wherein the antibody comprises a heavy chain sequence as shown in SEQ ID NO: 73 and a light chain sequence as shown in SEQ ID NO: 74.

7. A DNA molecule encoding the antibody or the antigen-binding fragment thereof according to claim 1.

8. A pharmaceutically acceptable expression vector comprising the DNA molecule according to claim 7.

9. A host cell comprising the DNA molecule according to claim 7.

10. A host cell comprising the expression vector according to claim 8.

11. A pharmaceutical composition comprising the antibody or the antigen-binding fragment thereof according to claim 1, and a plurality of pharmaceutically acceptable excipients, diluents, or carriers.

12. A method for treating MASP-2 related diseases in a subject in need of, comprising administering an effective amount of the antibody or the antigen-binding fragment thereof according to claim 1, wherein the disease is selected from the group consisting of IgA nephropathy, atypical hemolytic uremic syndrome, and hematopoietic stem cell transplantation-associated thrombotic microangiopathy.

13. A method for treating MASP-2 related diseases in a subject in need of, comprising administering an effective amount of the pharmaceutical composition according to claim 11, wherein the disease is selected from the group consisting of IgA nephropathy, atypical hemolytic uremic syndrome, and hematopoietic stem cell transplantation-associated thrombotic microangiopathy.

14. The antibody or the antigen-binding fragment thereof according to claim 1, wherein the antigen-binding fragment is selected from the group consisting of an Fab fragment, an Fab' fragment, an F(ab')2 fragment, an Fv fragment and an scFv fragment.

15. The method according to claim 12, wherein the disease is IgA nephropathy.

16. The method according to claim 13, wherein the disease is IgA nephropathy.

* * * * *

SEQUENCE LISTING

```
Sequence total quantity: 80
SEQ ID NO: 1              moltype = AA  length = 120
FEATURE                   Location/Qualifiers
source                    1..120
                          mol_type = protein
                          organism = Mus musculus
SEQUENCE: 1
```

```
QVQLQQSGAE LMKPGASVKI SCKATGYPFS TYWIEWVKQR PGHGLEWIGE ILPGSDNTNY    60
NEKFKGKATF TADTSSNTAY MQLSSLTSED SAVYYCARRT TATRAWFVYW GQGTLVTVSA   120

SEQ ID NO: 2           moltype = AA   length = 113
FEATURE                Location/Qualifiers
source                 1..113
                       mol_type = protein
                       organism = Mus musculus
SEQUENCE: 2
DIVMSQSPSS LAVSVGEKVT MSCKSSQSLL YSSNQKNYLA WYQQKPGQSP KLLIYWASTR    60
ESGVPDRFTG SGSGTDFTLT ISSVRAEDLA VYYCQHYYTY PWTFGGGTNL EIK          113

SEQ ID NO: 3           moltype = AA   length = 116
FEATURE                Location/Qualifiers
source                 1..116
                       mol_type = protein
                       organism = Mus musculus
SEQUENCE: 3
DVQLVESGGG LVQPGGSRKL SCAASGFTFS NFGIHWVRQA PEKGLEWVAY ISSGGSAVFY    60
ADTVKGRFTI SRDNSKNTLF LQMTSLRSED TAIYYCAKSD RYFDYWGQGT TLTVSS       116

SEQ ID NO: 4           moltype = AA   length = 111
FEATURE                Location/Qualifiers
source                 1..111
                       mol_type = protein
                       organism = Mus musculus
SEQUENCE: 4
DIVLTQSPAS LAVSLGQRAT ISCRASQSVS SSSYRYIHWY QQKPGQPPRL LIKYASNLES    60
GVPARFSGSG SGTDFTLNIH PVEEEDTATY YCQHSWETPW TFGGGTKLEI K            111

SEQ ID NO: 5           moltype = AA   length = 116
FEATURE                Location/Qualifiers
source                 1..116
                       mol_type = protein
                       organism = Mus musculus
SEQUENCE: 5
DVQLVESGGG LVQPGGSRKL SCAASGFTFS SFGMHWVRQA PEKGLEWVAY ISSGSSSFFY    60
ADTVKGRFTI SRDNPKNTLF LQMTSLRSED TAMYYCARGD RNFDVWGAGT TVTVSS       116

SEQ ID NO: 6           moltype = AA   length = 111
FEATURE                Location/Qualifiers
source                 1..111
                       mol_type = protein
                       organism = Mus musculus
SEQUENCE: 6
DIVLTQSPAS LAVSLGQRAT ISCRASQSVT SSRYSYMHWF QQKPGQPPNL LIKHASNLES    60
GVPARFSGSG SGTDFTLNIH PVEEDDTATY YCQHSWEVPW TFGGGTKLEI K            111

SEQ ID NO: 7           moltype = AA   length = 116
FEATURE                Location/Qualifiers
source                 1..116
                       mol_type = protein
                       organism = Mus musculus
SEQUENCE: 7
DVQLQESGPG LVKPSQSLSL TCTVTGYSIT SDYAWSWIRQ FLRNKLEWMG YISYSGRTSY    60
NPSLKSRISI TRDTSKNQFF LQLNSVTTED TATYFCARLI TGGDYWGQGT SVTVSS       116

SEQ ID NO: 8           moltype = AA   length = 107
FEATURE                Location/Qualifiers
source                 1..107
                       mol_type = protein
                       organism = Mus musculus
SEQUENCE: 8
DIVMTQSQKF MSTSVGDRVS VTCKASQNVG INVVWYQQKP GQSPKALIYS ASYRFSGVPD    60
RFTGSGSGTD FTLTISNVQS EDLAEYLCLQ YDINPLTFGA GTKLELK                 107

SEQ ID NO: 9           moltype = AA   length = 114
FEATURE                Location/Qualifiers
source                 1..114
                       mol_type = protein
                       organism = Mus musculus
SEQUENCE: 9
DVQLQESGPG LVKPSQSLSL TCTVTGYSIT SDYAWNWIRQ FPGNKLEWMG YISYSGRTSY    60
NPSLKSRLSI TRDTSKNQFF LQLTSVTTED TATYYCARHY GDFWGQGTTL TVSS         114

SEQ ID NO: 10          moltype = AA   length = 107
FEATURE                Location/Qualifiers
source                 1..107
                       mol_type = protein
```

```
                        organism = Mus musculus
SEQUENCE: 10
DIVMTQSQKF MSTSVGDRVS VTCKASQNVD TNVAWFQQKP GQSPKPLIYS ASYRYSGVPD    60
RFTGSGSGTD FTLTISNVQS EDLANYFCQQ YNSYPSTFGS GTKLEIK                107

SEQ ID NO: 11           moltype = AA   length = 116
FEATURE                 Location/Qualifiers
source                  1..116
                        mol_type = protein
                        organism = Mus musculus
SEQUENCE: 11
DVQLVESGGG LVQPGGSRKL SCVASGFTFS SFGMHWVRQA PEKGLEWVAY ISSGSSSSFY    60
VDTVKGRFTI SRDNPKNTLF LQMTSLRSED TAMYYCARGD RNFEVWGAGT TVTVSS       116

SEQ ID NO: 12           moltype = AA   length = 111
FEATURE                 Location/Qualifiers
source                  1..111
                        mol_type = protein
                        organism = Mus musculus
SEQUENCE: 12
DIVLTQSPAS LAVSLGQRAT ISCRASQSVS SSRYSYMHWF QQKPGQPPNL LIKHASNLES    60
GVPARFSGSG SGTDFTLNIH PVEEEDTATY YCQQSWEVPW TFGGGTKLEI K            111

SEQ ID NO: 13           moltype = AA   length = 117
FEATURE                 Location/Qualifiers
source                  1..117
                        mol_type = protein
                        organism = Mus musculus
SEQUENCE: 13
QVQLQQSGAE LAKPGASVKM SCKASGNTFT NYWMHWIKQR PGQGLEWVGY INPNTGYTDF    60
NQKFKDKATL TADKSSTTAY MQLISLTSED STVYYCTLQL GRNFDYWGQG TTLTVSS      117

SEQ ID NO: 14           moltype = AA   length = 111
FEATURE                 Location/Qualifiers
source                  1..111
                        mol_type = protein
                        organism = Mus musculus
SEQUENCE: 14
DIVLTQSPAS LGVSLGQRAT ISCRASQSVS SSRSTYIHWY QQKPGQPPKL LIKYSSNLES    60
GVPARFSGGG SGTDFTLNIH PVEAEDTATY YCHQSWEIPY TFGGGTKLEI R            111

SEQ ID NO: 15           moltype = AA   length = 5
FEATURE                 Location/Qualifiers
source                  1..5
                        mol_type = protein
                        organism = Mus musculus
SEQUENCE: 15
TYWIE                                                                 5

SEQ ID NO: 16           moltype = AA   length = 17
FEATURE                 Location/Qualifiers
source                  1..17
                        mol_type = protein
                        organism = Mus musculus
SEQUENCE: 16
EILPGSDNTN YNEKFKG                                                   17

SEQ ID NO: 17           moltype = AA   length = 11
FEATURE                 Location/Qualifiers
source                  1..11
                        mol_type = protein
                        organism = Mus musculus
SEQUENCE: 17
RTTATRAWFV Y                                                         11

SEQ ID NO: 18           moltype = AA   length = 17
FEATURE                 Location/Qualifiers
source                  1..17
                        mol_type = protein
                        organism = Mus musculus
SEQUENCE: 18
KSSQSLLYSS NQKNYLA                                                   17

SEQ ID NO: 19           moltype = AA   length = 7
FEATURE                 Location/Qualifiers
source                  1..7
                        mol_type = protein
                        organism = Mus musculus
SEQUENCE: 19
```

```
                                    -continued
WASTRES                                                                7

SEQ ID NO: 20           moltype = AA  length = 9
FEATURE                 Location/Qualifiers
source                  1..9
                        mol_type = protein
                        organism = Mus musculus SEQUENCE: 20
QHYYTYPWT                                                              9

SEQ ID NO: 21           moltype = AA  length = 5
FEATURE                 Location/Qualifiers
source                  1..5
                        mol_type = protein
                        organism = Mus musculus SEQUENCE: 21
NFGIH                                                                  5

SEQ ID NO: 22           moltype = AA  length = 17
FEATURE                 Location/Qualifiers
source                  1..17
                        mol_type = protein
                        organism = Mus musculus SEQUENCE: 22
YISSGGSAVF YADTVKG                                                    17

SEQ ID NO: 23           moltype = AA  length = 7
FEATURE                 Location/Qualifiers
source                  1..7
                        mol_type = protein
                        organism = Mus musculus SEQUENCE: 23
SDRYFDY                                                                7

SEQ ID NO: 24           moltype = AA  length = 15
FEATURE                 Location/Qualifiers
source                  1..15
                        mol_type = protein
                        organism = Mus musculus SEQUENCE: 24
RASQSVSSSS YRYIH                                                      15

SEQ ID NO: 25           moltype = AA  length = 7
FEATURE                 Location/Qualifiers
source                  1..7
                        mol_type = protein
                        organism = Mus musculus SEQUENCE: 25
YASNLES                                                                7

SEQ ID NO: 26           moltype = AA  length = 9
FEATURE                 Location/Qualifiers
source                  1..9
                        mol_type = protein
                        organism = Mus musculus SEQUENCE: 26
QHSWETPWT                                                              9

SEQ ID NO: 27           moltype = AA  length = 5
FEATURE                 Location/Qualifiers
source                  1..5
                        mol_type = protein
                        organism = Mus musculus SEQUENCE: 27
SFGMH                                                                  5

SEQ ID NO: 28           moltype = AA  length = 17
FEATURE                 Location/Qualifiers
source                  1..17
                        mol_type = protein
                        organism = Mus musculus SEQUENCE: 28
YISSGSSSFF YADTVKG                                                    17

SEQ ID NO: 29           moltype = AA  length = 7
FEATURE                 Location/Qualifiers
source                  1..7
                        mol_type = protein
                        organism = Mus musculus
```

```
SEQUENCE: 29
GDRNFDV                                                                7

SEQ ID NO: 30           moltype = AA  length = 15
FEATURE                 Location/Qualifiers
source                  1..15
                        mol_type = protein
                        organism = Mus musculus
SEQUENCE: 30
RASQSVTSSR YSYMH                                                      15

SEQ ID NO: 31           moltype = AA  length = 7
FEATURE                 Location/Qualifiers
source                  1..7
                        mol_type = protein
                        organism = Mus musculus
SEQUENCE: 31
HASNLES                                                                7

SEQ ID NO: 32           moltype = AA  length = 9
FEATURE                 Location/Qualifiers
source                  1..9
                        mol_type = protein
                        organism = Mus musculus
SEQUENCE: 32
QHSWEVPWT                                                              9

SEQ ID NO: 33           moltype = AA  length = 6
FEATURE                 Location/Qualifiers
source                  1..6
                        mol_type = protein
                        organism = Mus musculus
SEQUENCE: 33
SDYAWS                                                                 6

SEQ ID NO: 34           moltype = AA  length = 16
FEATURE                 Location/Qualifiers
source                  1..16
                        mol_type = protein
                        organism = Mus musculus
SEQUENCE: 34
YISYSGRTSY NPSLKS                                                     16

SEQ ID NO: 35           moltype = AA  length = 7
FEATURE                 Location/Qualifiers
source                  1..7
                        mol_type = protein
                        organism = Mus musculus
SEQUENCE: 35
LITGGDY                                                                7

SEQ ID NO: 36           moltype = AA  length = 11
FEATURE                 Location/Qualifiers
source                  1..11
                        mol_type = protein
                        organism = Mus musculus
SEQUENCE: 36
KASQNVGINV V                                                          11

SEQ ID NO: 37           moltype = AA  length = 7
FEATURE                 Location/Qualifiers
source                  1..7
                        mol_type = protein
                        organism = Mus musculus
SEQUENCE: 37
SASYRFS                                                                7

SEQ ID NO: 38           moltype = AA  length = 9
FEATURE                 Location/Qualifiers
source                  1..9
                        mol_type = protein
                        organism = Mus musculus
SEQUENCE: 38
LQYDINPLT                                                              9

SEQ ID NO: 39           moltype = AA  length = 6
FEATURE                 Location/Qualifiers
source                  1..6
                        mol_type = protein
```

```
                         organism = Mus musculus
SEQUENCE: 39
SDYAWN                                                                    6

SEQ ID NO: 40            moltype = AA  length = 16
FEATURE                  Location/Qualifiers
source                   1..16
                         mol_type = protein
                         organism = Mus musculus
SEQUENCE: 40
YISYSGRTSY NPSLKS                                                        16

SEQ ID NO: 41            moltype = AA  length = 5
FEATURE                  Location/Qualifiers
source                   1..5
                         mol_type = protein
                         organism = Mus musculus
SEQUENCE: 41
HYGDF                                                                     5

SEQ ID NO: 42            moltype = AA  length = 11
FEATURE                  Location/Qualifiers
source                   1..11
                         mol_type = protein
                         organism = Mus musculus
SEQUENCE: 42
KASQNVDTNV A                                                             11

SEQ ID NO: 43            moltype = AA  length = 7
FEATURE                  Location/Qualifiers
source                   1..7
                         mol_type = protein
                         organism = Mus musculus
SEQUENCE: 43
SASYRYS                                                                   7

SEQ ID NO: 44            moltype = AA  length = 9
FEATURE                  Location/Qualifiers
source                   1..9
                         mol_type = protein
                         organism = Mus musculus
SEQUENCE: 44
QQYNSYPST                                                                 9

SEQ ID NO: 45            moltype = AA  length = 5
FEATURE                  Location/Qualifiers
source                   1..5
                         mol_type = protein
                         organism = Mus musculus
SEQUENCE: 45
SFGMH                                                                     5

SEQ ID NO: 46            moltype = AA  length = 17
FEATURE                  Location/Qualifiers
source                   1..17
                         mol_type = protein
                         organism = Mus musculus
SEQUENCE: 46
YISSGSSSSF YVDTVKG                                                       17

SEQ ID NO: 47            moltype = AA  length = 7
FEATURE                  Location/Qualifiers
source                   1..7
                         mol_type = protein
                         organism = Mus musculus
SEQUENCE: 47
GDRNFEV                                                                   7

SEQ ID NO: 48            moltype = AA  length = 15
FEATURE                  Location/Qualifiers
source                   1..15
                         mol_type = protein
                         organism = Mus musculus
SEQUENCE: 48
RASQSVSSSR YSYMH                                                         15

SEQ ID NO: 49            moltype = AA  length = 7
FEATURE                  Location/Qualifiers
source                   1..7
```

```
                        mol_type = protein
                        organism = Mus musculus
SEQUENCE: 49
HASNLES                                                                7

SEQ ID NO: 50           moltype = AA  length = 9
FEATURE                 Location/Qualifiers
source                  1..9
                        mol_type = protein
                        organism = Mus musculus
SEQUENCE: 50
QQSWEVPWT                                                              9

SEQ ID NO: 51           moltype = AA  length = 5
FEATURE                 Location/Qualifiers
source                  1..5
                        mol_type = protein
                        organism = Mus musculus
SEQUENCE: 51
NYWMH                                                                  5

SEQ ID NO: 52           moltype = AA  length = 17
FEATURE                 Location/Qualifiers
source                  1..17
                        mol_type = protein
                        organism = Mus musculus
SEQUENCE: 52
YINPNTGYTD FNQKFKD                                                     17

SEQ ID NO: 53           moltype = AA  length = 8
FEATURE                 Location/Qualifiers
source                  1..8
                        mol_type = protein
                        organism = Mus musculus
SEQUENCE: 53
QLGRNFDY                                                               8

SEQ ID NO: 54           moltype = AA  length = 15
FEATURE                 Location/Qualifiers
source                  1..15
                        mol_type = protein
                        organism = Mus musculus
SEQUENCE: 54
RASQSVSSSR STYIH                                                       15

SEQ ID NO: 55           moltype = AA  length = 7
FEATURE                 Location/Qualifiers
source                  1..7
                        mol_type = protein
                        organism = Mus musculus
SEQUENCE: 55
YSSNLES                                                                7

SEQ ID NO: 56           moltype = AA  length = 9
FEATURE                 Location/Qualifiers
source                  1..9
                        mol_type = protein
                        organism = Mus musculus
SEQUENCE: 56
HQSWEIPYT                                                              9

SEQ ID NO: 57           moltype = DNA  length = 348
FEATURE                 Location/Qualifiers
source                  1..348
                        mol_type = other DNA
                        organism = synthetic construct
SEQUENCE: 57
caagtgcaac ttgtggaatc tggaggagga gtggtgcaac ctggaggatc tcttagactt   60
tcttgcgcag catctggatt tacattcagc aatttcggca tacattgggt gagacaagca  120
cctggaaagg gcctagaatg ggtggcatat atctcttctg gaggatctgc agtgttctac  180
gccgatacag tgaaaggaag atttacaatc tctagagata actctaagaa tacgcttat   240
cttcaaatga actctcttag agcagaagat acagcagtgt attattgcgc aaagagcgac  300
agatatttcg actactgggg gcagggaaca acagtgacag tgtcttct               348

SEQ ID NO: 58           moltype = AA  length = 116
FEATURE                 Location/Qualifiers
source                  1..116
                        mol_type = protein
                        organism = synthetic construct
```

```
SEQUENCE: 58
QVQLVESGGG VVQPGGSLRL SCAASGFTFS NFGIHWVRQA PGKGLEWVAY ISSGGSAVFY    60
ADTVKGRFTI SRDNSKNTLY LQMNSLRAED TAVYYCAKSD RYFDYWGQGT TVTVSS       116

SEQ ID NO: 59              moltype = DNA  length = 333
FEATURE                    Location/Qualifiers
source                     1..333
                           mol_type = other DNA
                           organism = synthetic construct
SEQUENCE: 59
gaaatcgtgc ttacacaatc tcctgctact ctaagtctga gtcctggaga aagagccacc    60
ctaagttgta gggcatctca atctgtgtct tcttcttctt atagatatat ccattggtat   120
caacagaagc ccgggcaagc acctagactt cttatctact atgcatctaa ccttgaatct   180
ggaatccctg caagattcag cgggtctgga tctggaacag atttcactttt gacaatctct  240
tctcttgaac ctgaagattt cgccgtttat tattgccaac attcttggga aacaccttgg   300
acatttggac aaggaacaaa gttagagatc aaa                                333

SEQ ID NO: 60              moltype = AA  length = 111
FEATURE                    Location/Qualifiers
source                     1..111
                           mol_type = protein
                           organism = synthetic construct
SEQUENCE: 60
EIVLTQSPAT LSLSPGERAT LSCRASQSVS SSSYRIHWY QQKPGQAPRL LIYYASNLES     60
GIPARFSGSG SGTDFTLTIS SLEPEDFAVY YCQHSWETPW TFGQGTKLEI K            111

SEQ ID NO: 61              moltype = AA  length = 443
FEATURE                    Location/Qualifiers
source                     1..443
                           mol_type = protein
                           organism = synthetic construct
SEQUENCE: 61
QVQLVESGGG VVQPGGSLRL SCAASGFTFS NFGIHWVRQA PGKGLEWVAY ISSGGSAVFY    60
ADTVKGRFTI SRDNSKNTLY LQMNSLRAED TAVYYCAKSD RYFDYWGQGT TVTVSSASTK   120
GPSVFPLAPC SRSTSESTAA LGCLVKDYFP EPVTVSWNSG ALTSGVHTFP AVLQSSGLYS   180
LSSVVTVPSS SLGTKTYTCN VDHKPSNTKV DKRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPS QEEMTKNQVS   360
LTCLVKGFYP SDIAVEWESN GQPENNYKTT PPVLDSDGSF FLYSRLTVDK SRWQEGNVFS   420
CSVLHEALHS HYTQKSLSLS LGK                                          443

SEQ ID NO: 62              moltype = AA  length = 218
FEATURE                    Location/Qualifiers
source                     1..218
                           mol_type = protein
                           organism = synthetic construct
SEQUENCE: 62
EIVLTQSPAT LSLSPGERAT LSCRASQSVS SSSYRIHWY QQKPGQAPRL LIYYASNLES     60
GIPARFSGSG SGTDFTLTIS SLEPEDFAVY YCQHSWETPW TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 63              moltype = DNA  length = 342
FEATURE                    Location/Qualifiers
source                     1..342
                           mol_type = other DNA
                           organism = synthetic construct
SEQUENCE: 63
caagtgcagc tgcaagagtc tggccctggc ctggtgaagc cttctcagac cctgagcctg    60
acctgcacag tgtctggcta cagcatcacc tctgactatg cctggaactg gatcagacag   120
cctcctggca agggcctgga gtggatgggc tacatcagct actctggcag aacaagctac   180
aaccctagct gaagagcag actgaccatc agcagagaca caagcaagaa tcagttcagc   240
ctgaagctga gctctgtgac agctgctgac acagctgtgt actactgtgc tagacactat   300
ggagactttct ggggccaagg caccacagtg acagtgagca gc                    342

SEQ ID NO: 64              moltype = AA  length = 114
FEATURE                    Location/Qualifiers
source                     1..114
                           mol_type = protein
                           organism = synthetic construct
SEQUENCE: 64
QVQLQESGPG LVKPSQTLSL TCTVSGYSIT SDYAWNWIRQ PPGKGLEWMG YISYSGRTSY    60
NPSLKSRLTI SRDTSKNQFS LKLSSVTAAD TAVYYCARHY GDFWGQGTTV TVSS         114

SEQ ID NO: 65              moltype = DNA  length = 321
FEATURE                    Location/Qualifiers
source                     1..321
                           mol_type = other DNA
                           organism = synthetic construct
```

```
SEQUENCE: 65
gacattcaga tgacacagag ccctagcagc ctgtctgcct ctgtgggaga cagagtgacc      60
atcacctgca aggcatctca gaatgtggac accaatgtgg cctggtatca gcagaagcct    120
ggcaaggccc ctaagctgct gatctactct gcaagctaca gatactctgg agtgcctagc    180
agattctctg gctctggctc tggcacagac ttcaccctga ccatcagcag cctgcagcct    240
gaggactttg ccacctacta ctgtcagcag tacaacagct accctagcac ctttggccaa    300
ggcaccaagc tggagatcaa g                                              321

SEQ ID NO: 66           moltype = AA  length = 107
FEATURE                 Location/Qualifiers
source                  1..107
                        mol_type = protein
                        organism = synthetic construct
SEQUENCE: 66
DIQMTQSPSS LSASVGDRVT ITCKASQNVD TNVAWYQQKP GKAPKLLIYS ASYRYSGVPS      60
RFSGSGSGTD FTLTISSLQP EDFATYYCQQ YNSYPSTFGQ GTKLEIK                  107

SEQ ID NO: 67           moltype = AA  length = 441
FEATURE                 Location/Qualifiers
source                  1..441
                        mol_type = protein
                        organism = synthetic construct
SEQUENCE: 67
QVQLQESGPG LVKPSQTLSL TCTVSGYSIT SDYAWNWIRQ PPGKGLEWMG YISYSGRTSY      60
NPSLKSRLTI SRDTSKNQFS LKLSSVTAAD TAVYYCARHY GDFWGQGTTV TVSSASTKGP    120
SVFPLAPCSR STSESTAALG CLVKDYFPEP VTVSWNSGAL TSGVHTFPAV LQSSGLYSLS    180
SVVTVPSSSL GTKTYTCNVD HKPSNTKVDK RVESKYGPPC PPCPAPEFLG GPSVFLFPPK    240
PKDTLMISRT PEVTCVVVDV SQEDPEVQFN WYVDGVEVHN AKTKPREEQF NSTYRVVSVL    300
TVLHQDWLNG KEYKCKVSNK GLPSSIEKTI SKAKGQPREP QVYTLPPSQE EMTKNQVSLT    360
CLVKGFYPSD IAVEWESNGQ PENNYKTTPP VLDSDGSFFL YSRLTVDKSR WQEGNVFSCS    420
VLHEALHSHY TQKSLSLSLG K                                              441

SEQ ID NO: 68           moltype = AA  length = 214
FEATURE                 Location/Qualifiers
source                  1..214
                        mol_type = protein
                        organism = synthetic construct
SEQUENCE: 68
DIQMTQSPSS LSASVGDRVT ITCKASQNVD TNVAWYQQKP GKAPKLLIYS ASYRYSGVPS      60
RFSGSGSGTD FTLTISSLQP EDFATYYCQQ YNSYPSTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 69           moltype = DNA  length = 348
FEATURE                 Location/Qualifiers
source                  1..348
                        mol_type = other DNA
                        organism = synthetic construct
SEQUENCE: 69
caagtgcaac ttgtggaatc tggaggagga gtggtgcaac ctggaagatc tcttagactt      60
tcttgcgcag catctggatt tacattcagt tcgttcggca tgcattgggt gagacaagca    120
cctggaaagg gcctgaatg ggtggcatat atctcttctg gatcttcttc ttctttctac    180
gtcgatacag tgaaaggaag atttacaatc tctagagata actctaagaa tacgctttat    240
cttcaaatga actctcttag agcagaagat acagcagtgt attattgcgc aagaggagat    300
agaaactttg aagtgtgggg tcaggggaca acagtgacag tgtcttct                 348

SEQ ID NO: 70           moltype = AA  length = 116
FEATURE                 Location/Qualifiers
source                  1..116
                        mol_type = protein
                        organism = synthetic construct
SEQUENCE: 70
QVQLVESGGG VVQPGRSLRL SCAASGFTFS SFGMHWVRQA PGKGLEWVAY ISSGSSSSFY      60
VDTVKGRFTI SRDNSKNTLY LQMNSLRAED TAVYYCARGD RNFEVWGQGT TVTVSS        116

SEQ ID NO: 71           moltype = DNA  length = 333
FEATURE                 Location/Qualifiers
source                  1..333
                        mol_type = other DNA
                        organism = synthetic construct
SEQUENCE: 71
gatatccaga tgactcagag ccctagcagc ctgagcgcca gcgtgggcga tagggtgact      60
atcacttgta gggccagcca gagcgtgagc agcagcaggt acagctacat gcactggttc    120
cagcagaagc ctggcaaggc tcctaagctg ctgatctacc acgccagcaa tctggagagc    180
ggcgtgccta gcaggttcag cggcagcggc agcggcactg atttcactct gactatcagc    240
agcctgcagc ctgaggattt cgccacttac tactgtcagc agagctggga ggtgccttgg    300
actttcggcc agggcactaa gctggagatc aag                                 333

SEQ ID NO: 72           moltype = AA  length = 111
```

| FEATURE | Location/Qualifiers |
|---|---|
| source | 1..111<br>mol_type = protein<br>organism = synthetic construct |

SEQUENCE: 72
```
DIQMTQSPSS LSASVGDRVT ITCRASQSVS SSRYSMHWF QQKPGKAPKL LIYHASNLES   60
GVPSRFSGSG SGTDFTLTIS SLQPEDFATY YCQQSWEVPW TFGQGTKLEI K          111
```

| SEQ ID NO: 73 | moltype = AA length = 443 |
|---|---|
| FEATURE | Location/Qualifiers |
| source | 1..443<br>mol_type = protein<br>organism = synthetic construct |

SEQUENCE: 73
```
QVQLVESGGG VVQPGRSLRL SCAASGFTFS SFGMHWVRQA PGKGLEWVAY ISSGSSSSFY   60
VDTVKGRFTI SRDNSKNTLY LQMNSLRAED TAVYYCARGD RNFEVWGQGT TVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF LGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVLHEALHS HYTQKSLSLS LGK                                          443
```

| SEQ ID NO: 74 | moltype = AA length = 218 |
|---|---|
| FEATURE | Location/Qualifiers |
| source | 1..218<br>mol_type = protein<br>organism = synthetic construct |

SEQUENCE: 74
```
DIQMTQSPSS LSASVGDRVT ITCRASQSVS SSRYSMHWF QQKPGKAPKL LIYHASNLES   60
GVPSRFSGSG SGTDFTLTIS SLQPEDFATY YCQQSWEVPW TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218
```

| SEQ ID NO: 75 | moltype = DNA length = 351 |
|---|---|
| FEATURE | Location/Qualifiers |
| source | 1..351<br>mol_type = other DNA<br>organism = synthetic construct |

SEQUENCE: 75
```
caagtgcaac ttgtgcaatc tggagcagaa gtgaagaagc caggtgcatc tgtgaaagtg   60
tcttgcaaag catctggaaa cacatttaca aactattgga tgcattggat cagacaagca  120
cctggacaag gacttgaatg gatgggatac attaatccca acgggactta cactgactat  180
aaccagaaat ttaaagatag agtaacactt acagcagata atctacaag cacagcatat   240
atggaacttt cttctcttag atctgaagat acagcagtgt attattgcac acttcaactt  300
ggaagaaact ttgattattg gggccagggc acaacagtga cagtgtcttc t           351
```

| SEQ ID NO: 76 | moltype = AA length = 117 |
|---|---|
| FEATURE | Location/Qualifiers |
| source | 1..117<br>mol_type = protein<br>organism = synthetic construct |

SEQUENCE: 76
```
QVQLVQSGAE VKKPGASVKV SCKASGNTFT NYWMHWIRQA PGQGLEWMGY INPNTGYTDF   60
NQKFKDRVTL TADKSTSTAY MELSSLRSED TAVYYCTLQL GRNFDYWGQG TTVTVSS      117
```

| SEQ ID NO: 77 | moltype = DNA length = 333 |
|---|---|
| FEATURE | Location/Qualifiers |
| source | 1..333<br>mol_type = other DNA<br>organism = synthetic construct |

SEQUENCE: 77
```
gatatccaaa tgacacaatc tccttcttct ctttctgcat ctgtgggaga tagagtgaca   60
atcacatgca gagcatctca atctgtgtct tcttctagat ctacatatat ccattggtat  120
caacagaagc cgggcaaggc tccgaaacta ttgatctact attcttctaa ccttgaatct  180
ggagtgcctt ctagattctc aggttctgga tctggaacag atttcacctt aacaatctct  240
tctcttcaac tgaagatttt cgcgacgtat tattgccatc aatcttggga aatcccttat  300
acatttggac aaggaacaaa gttagagatc aaa                                333
```

| SEQ ID NO: 78 | moltype = AA length = 111 |
|---|---|
| FEATURE | Location/Qualifiers |
| source | 1..111<br>mol_type = protein<br>organism = synthetic construct |

SEQUENCE: 78
```
DIQMTQSPSS LSASVGDRVT ITCRASQSVS SSRSTYIHWY QQKPGKAPKL LIYYSSNLES   60
GVPSRFSGSG SGTDFTLTIS SLQPEDFATY YCHQSWEIPY TFGQGTKLEI K           111
```

| SEQ ID NO: 79 | moltype = AA length = 444 |
|---|---|

```
FEATURE              Location/Qualifiers
source               1..444
                     mol_type = protein
                     organism = synthetic construct
SEQUENCE: 79
QVQLVQSGAE VKKPGASVKV SCKASGNTFT NYWMHWIRQA PGQGLEWMGY INPNTGYTDF    60
NQKFKDRVTL TADKSTSTAY MELSSLRSED TAVYYCTLQL GRNFDYWGQG TTVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVLHEALH SHYTQKSLSL SLGK                                         444

SEQ ID NO: 80        moltype = AA  length = 218
FEATURE              Location/Qualifiers
source               1..218
                     mol_type = protein
                     organism = synthetic construct
SEQUENCE: 80
DIQMTQSPSS LSASVGDRVT ITCRASQSVS SSRSTYIHWY QQKPGKAPKL LIYYSSNLES    60
GVPSRFSGSG SGTDFTLTIS SLQPEDFATY YCHQSWEIPY TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218
```